(12) United States Patent
Isogai et al.

(10) Patent No.: US 10,238,281 B2
(45) Date of Patent: Mar. 26, 2019

(54) OPTICAL COHERENCE TOMOGRAPHY DEVICE

(71) Applicant: NIDEK CO., LTD., Gamagori, Aichi (JP)

(72) Inventors: Naoki Isogai, Nishio (JP); Hideki Aono, Gamagori (JP); Yukihiro Higuchi, Toyota (JP); Yuji Murase, Gamagori (JP); Norimasa Satake, Nukata-gun (JP); Keiji Murata, Gamagori (JP)

(73) Assignee: NIDEK CO., LTD., Gamagori-shi (JP)

( * ) Notice: Subject to any disclaimer, the term of this patent is extended or adjusted under 35 U.S.C. 154(b) by 60 days.

(21) Appl. No.: 15/422,866

(22) Filed: Feb. 2, 2017

(65) Prior Publication Data
US 2017/0238798 A1    Aug. 24, 2017

(30) Foreign Application Priority Data

Feb. 3, 2016 (JP) .................................. 2016-019365
Jan. 31, 2017 (JP) .................................. 2017-016370

(51) Int. Cl.
*A61B 3/10* (2006.01)
*A61B 3/12* (2006.01)
*A61B 3/00* (2006.01)
*A61F 9/008* (2006.01)

(52) U.S. Cl.
CPC ............ *A61B 3/102* (2013.01); *A61B 3/0008* (2013.01); *A61B 3/0025* (2013.01); *A61B 3/0058* (2013.01); *A61B 3/1005* (2013.01); *A61B 3/1233* (2013.01); *A61B 3/1241* (2013.01); *A61F 9/00821* (2013.01); *A61F 2009/00851* (2013.01)

(58) Field of Classification Search
CPC ..... A61B 3/102; A61B 3/0008; A61B 3/0025; A61B 3/0058; A61B 3/1233; A61B 3/1241; A61B 3/1005; A61F 9/00821
See application file for complete search history.

(56) References Cited

PUBLICATIONS

Wieser et al., "High definition live 3D-OCT in vivo: design and evaluation of a 4D OCT engine with 1 GVoxel/s", Biomedical Optics Express, vol. 5, No. 9, 2014.

*Primary Examiner* — Jack Dinh
(74) *Attorney, Agent, or Firm* — Oliff PLC

(57) ABSTRACT

An optical coherence tomography device includes an OCT optical system that irradiates a tissue of the subject's eye with measurement light from a light source, and detects interference between reference light and the measurement light reflected from the tissue by using a detector, and a processor, in which the processor performs a generation process of acquiring A-scan data based on a signal output from the detector in a cycle of 300 kilohertz or more and generating three-dimensional OCT data at any time based on the acquired A-scan data, and performs an analysis process on each piece of the three-dimensional OCT data generated at any time through the generation process, so as to output a real-time analysis result of the three-dimensional OCT data which is generated at any time.

14 Claims, 6 Drawing Sheets

OPTICAL COHERENCE TOMOGRAPHY DEVICE

CROSS REFERENCE TO RELATED APPLICATIONS

This application is based upon and claims the benefit of priorities of Japanese Patent Application No. 2016-019365 filed on Feb. 3, 2016 and Japanese Patent Application No. 2017-016370 filed on Jan. 31, 2017, the contents of which are incorporated herein by reference in its entirety.

TECHNICAL FIELD

The present disclosure relates to an optical coherence tomography device acquiring OCT data of the subject's eye according to an optical coherence principle.

In order to acquire information regarding the subject's eye in a depth direction, an optical coherence tomography device (OCT device) is used in an ophthalmological field. As an optical coherence tomography device, in the related art, there is a device which can scan a tissue of the subject's eye with measurement light in a two-dimensional manner by driving an optical scanner (for example, refer to JP-A-2016-13210).

A galvanomirror has a feature that the controllability and the degree of freedom in a scanning pattern are high, and is thus used as a typical optical scanner in an optical coherence tomography device.

In recent years, in the technical field of the optical coherence tomography device, a device which can perform an A-scan operation at a high speed has been proposed. Consequently, three-dimensional OCT data can be obtained at a wider angle of view or at a higher frame rate (for example, refer to Wieser, W., Draxinger, W., Klein, T., Karpf, S., Pfeiffer, T., und Huber, R.: High definition live 3D-OCT in vivo: design and evaluation of a 4D OCT engine with 1 GVoxel/s. Biomedical Optics Express, vol. 5, no. 9, pp. 2963-77, September, 2014).

SUMMARY OF THE INVENTION

In the ophthalmological field, a method of applying the optical coherence tomography device performing an A-scan operation at a high speed has not been examined sufficiently yet.

In the related art, in the optical coherence tomography device, a galvanomirror is operated in a range of 100 Hz at most even if used for main scanning, driving conditions in a case where the galvanomirror is operated at a higher speed than 100 Hz have not been examined sufficiently.

An object of the present disclosure is to provide an optical coherence tomography device capable of solving at least one of the above-described problems.

According to an aspect of the present disclosure, there is provided an optical coherence tomography device including an OCT optical system that irradiates a tissue of the subject's eye with measurement light from a light source, and detects interference between reference light and the measurement light reflected from the tissue by using a detector; and a processor, in which the processor performs a generation process of acquiring A-scan data based on a signal output from the detector in a cycle of 300 kilohertz or more and generating three-dimensional OCT data at any time on the basis of the acquired A-scan data, and performs an analysis process on each piece of the three-dimensional OCT data generated at any time through the generation process, so as to output a real-time analysis result of the three-dimensional OCT data which is generated at any time.

According to another aspect of the present disclosure, there is provided an optical coherence tomography device including an OCT optical system that irradiates a tissue of the subject's eye with measurement light from a light source, and detects interference between reference light and the measurement light reflected from the tissue by using a detector; and a processor, in which the processor performs a generation process of acquiring A-scan data based on a signal output from the detector in a cycle of 300 kilohertz or more and generating three-dimensional OCT data at any time on the basis of the acquired A-scan data, and a display control process of generating a two-dimensional image indicating a section in an acquisition range of the three-dimensional OCT data as a graphics in which the three-dimensional OCT data is visualized on the basis of each piece of the three-dimensional OCT data generated at any time through the generation process, and updating and displaying the generated two-dimensional image on a monitor.

According to still another aspect of the present disclosure, there is provided an optical coherence tomography device including an OCT optical system that irradiates a tissue of the subject's eye with measurement light from a light source, and detects interference between reference light and the measurement light reflected from the tissue by using a detector; a scanning unit that includes an optical scanner for main scanning that includes one or a plurality of galvanomirrors which scan the subject's eye with the measurement light in a predetermined main scanning direction by performing reciprocation driving formed of forward moving and backward moving, and an optical scanner for sub-scanning that is different from the optical scanner for main scanning in terms of a scanning direction, and scans the subject's eye with the measurement light in a two-dimensional manner on the basis of operations of the optical scanner for main scanning and the optical scanner for sub-scanning; and a processor, in which the processor acquires A-scan data based on a signal output from the detector in a cycle of 300 kilohertz or more, performs scanning with measurement light continuously twice or more in the main scanning direction by repeatedly reciprocating the galvanomirror at a constant swing angle, and controls at least the galvanomirror so that a time difference between start timings of respective scanning operations is set to a value which is equal to or less than 5 milliseconds.

BEST MODE FOR CARRYING OUT THE INVENTION

Figure 1:
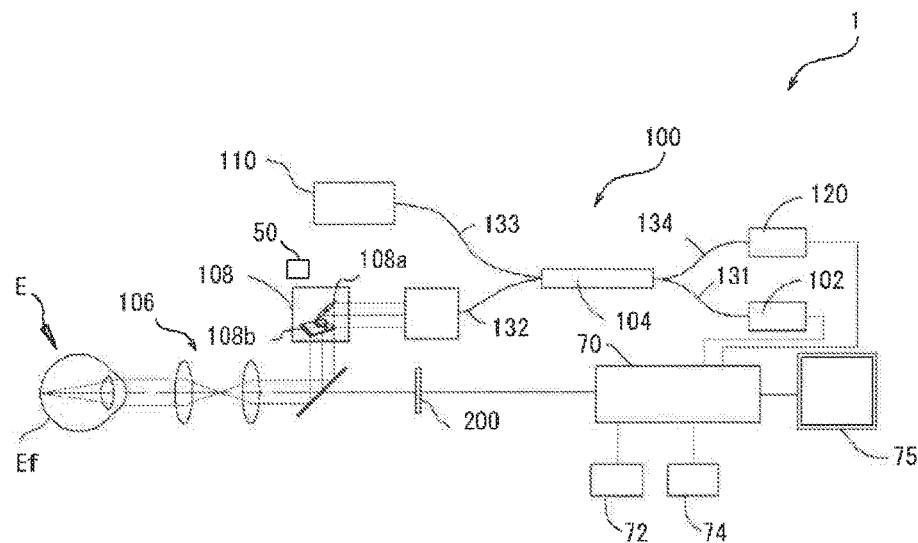
FIG. 1 is a block diagram illustrating a schematic configuration of an optical coherence tomography device according to an embodiment.

Hereinafter, an exemplary embodiment related to the present disclosure will be described with reference to the drawings. FIG. 1 illustrates a schematic configuration of an optical coherence tomography device 1 (hereinafter, referred to as an "OCT 1") of the present embodiment. In the present embodiment, the OCT 1 performs an A-scanning operation in a cycle of 300 kilohertz or more.

In the present embodiment, the OCT 1 may be Fourier domain OCT (FD-OCT). Hereinafter, the description will be made assuming that the OCT 1 is a swept source OCT (SS-OCT) which is one kind of the FD-OCT. In this case, the OCT 1 includes a wavelength sweeping light source which temporally sweeps an emitted wavelength as a light source, and includes a point detector as a detector. The point detector may be a single detector, and may be a balance detector which performs balance detection by using a plurality of (for example, two) detectors. The OCT 1 samples interference signals for return light beams of reference light and measurement light according to a change in an emitted wavelength from the wavelength sweeping light source, and obtains OCT data of the subject's eye on the basis of an interference signal at each wavelength, obtained through the sampling.

<Optical System>

The OCT 1 exemplified in FIG. 1 includes an OCT optical system 100 and a fixation optical system 200. The fixation optical system 200 projects a fixation target onto the subject's eye.

The OCT optical system 100 mainly includes a light source 102, an optical scanner 108, and a detector 120. As illustrated in FIG. 1, the OCT 1 includes a light splitter/combiner 104 and a reference optical system 110. In the example illustrated in FIG. 1, solid lines 131 to 134 connecting respective portions to each other indicate light guide optical fibers.

As the light source 102, a wavelength variable light source (wavelength scanning light source) which temporally changes an emitted wavelength is used. The light source 102 performs scanning with a wavelength in a cycle of, for example, 300 kilohertz or more. Consequently, the OCT 1 can acquire A-scan data (details thereof will be described later) in a cycle of 300 kilohertz or more. The term "300 kilohertz or more" mentioned here may include a case where an A-scan operation is performed in a cycle of, for example, 1 megahertz or more. Such a light source may be, for example, a Fourier domain mode locking (FDML) laser device. The FDML laser device is one kind of the wavelength sweeping light source. The FDML laser device may have a structure in which, for example, a wavelength sweeping filter, a dispersion compensation mechanism for reducing the influence of dispersion characteristics, and the like are incorporated into a resonator including a gain medium. A wavelength selection filter may be a filter using, for example, a combination of a diffraction grating and a polygon mirror, or a Fabry-Perot etalon (for example, JP-A-2012-222164 filed by the present applicant). The light source 102 is not necessarily required to be the FDML laser device, and may be a light source which performs scanning with a wavelength in a cycle of 300 kilohertz or more according to a principle which is different from that of the FDML laser device.

As the detector 120 illustrated in FIG. 1, a balance detector formed of, for example, a light receiving element may be provided. The light receiving element is a point sensor formed of only one light receiving portion, and, for example, an avalanche photodiode is used.

The light splitter/combiner 104 illustrated in FIG. 1 functions as both a light splitter and a light combiner. As the light splitter, the light splitter/combiner 104 splits light emitted from the light source 102 into measurement light and reference light. As a result, the measurement light is guided to the fundus Ef via the optical scanner 108, and the reference light is guided to the reference optical system 110 (details thereof will be described later). As the light combiner, the light splitter/combiner 104 combines the measurement light reflected from the fundus Ef and the reference light. As will be described later in detail, interference light acquired by combining the measurement light reflected from the fundus Ef and the reference light is received by the detector (light receiving element) 120. As an example of the light splitter/combiner 104, a fiber coupler is used in FIG. 1.

In the present embodiment, some light (measurement light) as a result of splitting in the light splitter/combiner 104 is first incident to an optical fiber 132. The measurement light incident to the optical fiber 132 is converted into parallel light by a collimator lens (not illustrated), and is then incident to the optical scanner 108.

Figure 2:
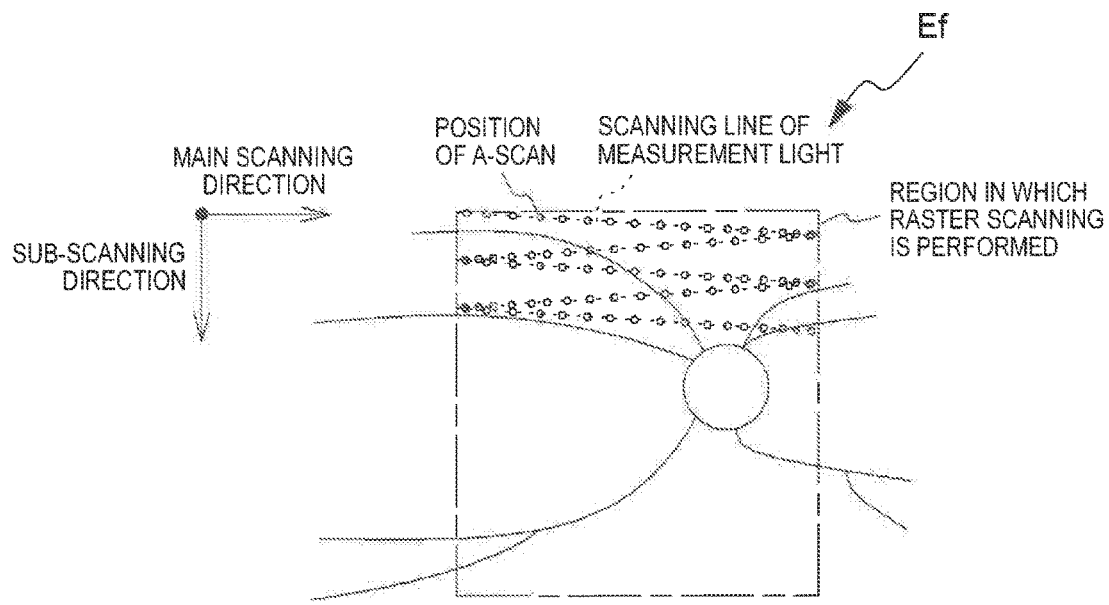
FIG. 2 is a diagram for explaining raster scanning performed on the fundus.

The optical scanner 108 is used to scan the fundus Ef with the measurement light from the light source 102. The optical scanner 108 scans the fundus Ef with the measurement light in xy directions (crossing directions). In the present embodiment, the optical scanner 108 performs raster scanning with the measurement light on the fundus. In the present embodiment, raster scanning as exemplified in FIG. 2 is periodically performed in a predetermined region (a position and an area are constant) of the fundus.

The optical scanner 108 is disposed at a position substantially conjugate to the pupil. The optical scanner 108 is operated on the basis of a control signal which is input to a driver 50.

As the optical scanner 108 of the present embodiment, for example, not only a reflective mirror (a galvanomirror, a polygon mirror, a resonant scanner, a MEMS mirror) but also an acousto-optical modulator (AOM) which changes a traveling (deflection) direction of light may be used. For example, the optical scanner 108 illustrated in FIG. 1 includes two scanners such as an optical scanner 108a for main scanning and an optical scanner 108b for sub-scanning. Two optical scanners 108a and 108b perform scanning with light in different directions. For example, the optical scanner 108a may perform scanning with light in the x direction, and the optical scanner 108b may perform scanning with light in the y direction. In the present embodiment, preferably, the optical scanner 108a for main scanning can perform scanning in a cycle of, for example, at least kHz order. In the example illustrated in FIG. 1, a resonant scanner is used as an example of the optical scanner 108a satisfying such a condition. However, the resonant scanner is only an example, and other optical scanners such as a polygon mirror or an AOM may be used as the optical scanner 108a for main scanning. On the other hand, preferably, the optical scanner 108b for sub-scanning can perform scanning in a cycle of at least several tens of Hz order. In the example illustrated in FIG. 1, a galvanomirror is used as an example of the optical scanner 108b satisfying such a condition. However, the galvanomirror is only an example, and other optical scanners such as an AOM may be used as the optical scanner 108b for sub-scanning. Main scanning and sub-scanning are not required to be performed by separate optical scanners. For example, main scanning and sub-scanning may be performed by a single optical scanner. In other words, a scanner performing optical scanning related to two axes may be applied to the optical scanner 108.

In the present embodiment, the two scanners 108a and 108b periodically perform raster scanning with the measurement light in a region (a region having a constant area) of the fundus. The measurement light deflected by the optical scanner 108 is applied to the fundus Ef through an objective optical system 106.

Backscattering light (reflected light) of the measurement light from the fundus Ef reversely follows the optical path during light emission, and is guided to the light splitter/combiner 104. The reflected light is combined and interferes with reference light in the light splitter/combiner 104.

The reference optical system 110 generates reference light which is combined with reflected light obtained by reflection of measurement light on the fundus Ef. The reference optical system 110 may be of a Michelson type, and may be of a Mach-Zenhder type. The reference optical system 110 is formed of, for example, a reflection optical system (for example, a reference mirror), and reflects light from the light splitter/combiner 104 with the reflection optical system so that the light is guided to the detector 120 through the light splitter/combiner 104. As another example, the reference optical system 110 may be formed of a transmission optical system (for example, an optical fiber), and may transmit light from the light splitter/combiner 104 through the transmission optical system without returning the light so that the light is guided to the detector 120.

The OCT 1 moves at least some optical members disposed in the OCT optical system 100 in an optical axis direction in order to adjust an optical path length difference between measurement light and reference light. For example, the reference optical system 110 has a configuration of adjusting an optical path length difference between measurement light and reference light by moving an optical member (for example, a reference mirror) on a reference optical path. For example, the reference mirror is moved in the optical axis direction through driving in a driving mechanism. The configuration of changing an optical path length difference may be disposed on a measurement optical path of a measurement optical system 20. An optical member (for example, an end of an optical fiber) disposed on the measurement optical path is moved in the optical axis direction.

The interference signal light obtained by combining the measurement light and the reference light is incident to the detector 120 via the light splitter/combiner 104 and a fiber 134. Consequently, the detector 120 detects the interference signal light.

If an emitted wavelength is changed by the light source 102, interference signal light corresponding thereto is received by the detector 120, and, as a result, the interference signal light is received as spectral interference signal light by the detector 120. A spectral interference signal (also referred to as an OCT signal) output from the detector 120 is received by a control unit 70. A depth profile is formed on the basis of the spectral interference signal.

<Control System>

Next, with reference to FIG. 1, a control system of the OCT 1 will be described. The OCT 1 mainly includes the control unit 70 and a memory (storage unit) 71 as the control system.

In the present embodiment, the control unit 70 is a processor in the OCT 1. The control unit 70 is formed of, for example, a central processing unit (CPU) and a memory (for example, a RAM and a ROM). The control unit 70 controls an operation of each portion of the OCT 1. For example, the control unit 70 controls the optical scanner 108 so that raster scanning with measurement light is repeatedly performed on the fundus. OCT data of the subject's eye is acquired on the basis of a signal which is output from the detector 120 as a result of the raster scanning (details thereof will be described later). The OCT data mentioned here may be any one of one-dimensional OCT data, two-dimensional OCT data, and three-dimensional OCT data. In the example illustrated in FIG. 1, the control unit 70 is also used as an image processing unit. For example, the control unit 70 may include an image processing IC which can perform various processes on the OCT data.

The memory 72 is a rewritable nonvolatile storage medium. As the memory 72, for example, any one of a hard disk, a flash memory, an external server, and a USB memory may be used. In the present embodiment, the memory 72 stores the OCT data, analysis results of the OCT data, and the like.

As illustrated in FIG. 1, the OCT 1 may include an operation unit (input interface) 74, and a monitor 75. The respective portions illustrated in FIG. 1 are connected to each other via a network (a bus, a LAN, or the like), and can transmit and receive data (for example, image data) to and from each other.

The operation unit 74 receives an operation from an examiner. As the operation unit 74, for example, a device such as a mouse, a track ball, or a touch panel may be used. The operation unit 74 is not limited to such a contact type device, and may employ a device such a motion sensor which receives an operation in a noncontact manner.

The monitor 75 displays graphics (for example, a tomographic image) obtained by visualizing OCT data, layer thickness information, and the like. In the present embodiment, display control for the monitor 75 is performed by the control unit 70. In other words, in the present embodiment, the control unit 70 is also used as a display control unit. The monitor 75 may be, for example, a touch panel. In this case, the monitor 75 functions as a part of the operation unit 74. The monitor 75 may be a device provided with a two-dimensional screen. In this case, the device may be any one of a cradle type, a carrying type, or a mounting type (for example, a head mounted display). A projection type device projecting an image onto a screen may be used. The monitor 75 may be a three-dimensional display displaying a three-dimensional image. As an example, the projection type device may be a volume type display which projects a three-dimensional image into a space.

<Description of Operation>

Hereinafter, a description will be made of an operation of the apparatus having the above-described configuration.

<Operation of Acquiring Three-Dimensional OCT Data>

For example, the control unit 70 acquires A-scan data (an example of one-dimensional OCT data) based on a signal output from the detector 120 in a cycle of 300 kilohertz or more. In the present embodiment, A-scan data of one cycle is information regarding a tissue in a depth direction (optical axis direction) at one point on the fundus. The A-scan data may be a complex OCT signal obtained by performing Fourier transform on a signal (OCT signal) output from the detector 120. The A-scan data may be a depth profile obtained by further processing the complex OCT signal.

In the present embodiment, the control unit 70 may acquire A-scan data in synchronization with a cycle of a wavelength change in the light source 102. Consequently, A-scan data at a plurality of points is acquired for each scanning line (refer to FIG. 2). For example, there may be a configuration in which a clock signal having a cycle of 300 kilohertz or more is input to both of the light source 102 and the control unit 70, and wavelength scanning in the light source 102 and acquisition of A-scan data in the control unit 70 are performed in a cycle of 300 kilohertz or more in synchronization with each other.

In the present embodiment, three-dimensional OCT data is acquired by the control unit 70 on the basis of the A-scan data at a plurality of points. The three-dimensional OCT data in the present embodiment is information regarding a three-dimensional tissue in a range of raster scanning. Three-dimensional OCT data of one unit (in other words, one frame) is obtained on the basis of raster scanning of at least one cycle. For example, three-dimensional OCT data of one frame may include a plurality of pieces of A-scan data acquired through raster scanning of one cycle. In the present embodiment, the control unit 70 generates three-dimensional OCT data based on raster scanning whenever the raster scanning of one cycle is performed. For example, data formed by two-dimensionally arranging depth profiles (an example of A-scan data) in the xy directions may be three-dimensional OCT data. As mentioned above, in the present embodiment, three-dimensional OCT data of one unit (in other words, one frame) is formed on the basis of interference signals which are output from the detector 120 as results of raster scanning of one cycle.

A frame rate for generating three-dimensional OCT data may be set as appropriate. For example, if raster scanning is performed in a cycle of about 8 Hz, three-dimensional OCT data in a range of raster scanning may be generated at a frame rate of about 8 fps. In this case, assuming that A-scan data is acquired at about 300 kilohertz, three-dimensional OCT data of one frame is built on the basis of A-scan data obtained on the basis of points of about 200×200 in xy directions of the fundus. The number of points (that is, the number of points in a single piece of A-scan data) in the depth direction in the three-dimensional OCT data depends on, for example, a spectral width of measurement light. For example, A-scan data formed of the number of points such as about 200 points in the depth direction may be acquired.

<Display of Image Based on Three-Dimensional OCT Data>

The control unit 70 updates and displays graphics obtained by visualizing three-dimensional OCT data which is generated at any time on the monitor 75. In the present embodiment, whenever new three-dimensional OCT data is acquired, the control unit 70 updates graphics displayed on the monitor 75 to graphics obtained by visualizing the new three-dimensional OCT data. In other words, in the present embodiment, a moving image indicating a tissue (for example, a three-dimensional tissue of the fundus) of the subject's eye E in real time is displayed on the monitor 75. As a result, a dynamic state of the tissue of the fundus in real time can be observed by using the moving image.

In the present embodiment, the term "real time" is assumed to indicate that a change in the subject's eye at each time point is reflected on an image, information, and the like at the substantially same time.

<Three-Dimensional Image Display Process>

Figure 3:
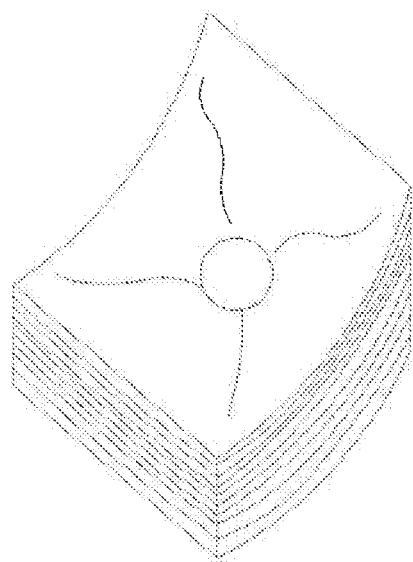
FIG. 3 is a schematic diagram illustrating a three-dimensional image.

The graphics obtained by visualizing three-dimensional OCT data may be three-dimensional images as illustrated in FIG. 3, for example. The three-dimensional images may be images in which, for example, two-dimensional reflection intensity distributions (for example, tomographic images) in each scanning line are arranged in a sub-scanning direction (a direction intersecting the scanning line). In other words, the three-dimensional images may be images indicating three-dimensional reflection intensity distributions (for convenience, such images will be referred to as three-dimensional OCT images). A three-dimensional OCT image may be a three-dimensional motion contrast image. The motion contrast is detection information regarding a motion or a temporal change of a subject (subject's eye). For example, a flow image is assumed to be one kind of motion contrast. The flow image is an image obtained by detecting a motion of, for example, a fluid. It can be said that a blood vessel angiographic image (OCT angiography) in which a blood vessel position obtained by detecting a motion of blood is imaged is one kind of the motion contrast. A specific example of a process of acquiring a three-dimensional motion contrast image will be described later.

<Process of Displaying Tomographic Image of any Section>

Graphics obtained by visualizing three-dimensional OCT data may be a tomographic image. For example, a two-dimensional image based on a signal intensity distribution at any section in an acquisition range of three-dimensional OCT data may be generated as a tomographic image by the control unit 70. For example, the tomographic image is not limited to indicating a section in a certain scanning line. For example, an image indicating a section obliquely crossing a plurality of scanning lines may be formed as a tomographic image by the control unit 70. A section related to a tomographic image may be a planar surface or a curved surface. A tomographic image may be a motion contrast image.

For example, in the present embodiment, a real-time tomographic image of a certain section may be displayed on the monitor 75. A position of a section may be defined in advance. A position of a section may be a position selected by the control unit 70 from an acquisition range of three-dimensional OCT data on the basis of a signal from the operation unit 74 (selection process). The signal from the operation unit 74 may be a signal for designating a section desired by an examiner. As a result of a position of a section being selected on the basis of the signal from the operation unit 74, a tomographic image indicating the section corresponding to the selected position is displayed on the monitor 75 by the control unit 70. Thus, a state of a tissue in the desired section can be observed from a real-time tomographic image which is generated on the basis of three-dimensional OCT data.

Here, with reference to the drawings, a description will be made of a specific example of an operation of the device in a case where a position of a section displayed as a tomographic image is selected from the acquisition range of three-dimensional OCT data on the basis of a signal from the operation unit 74.

Figure 5:
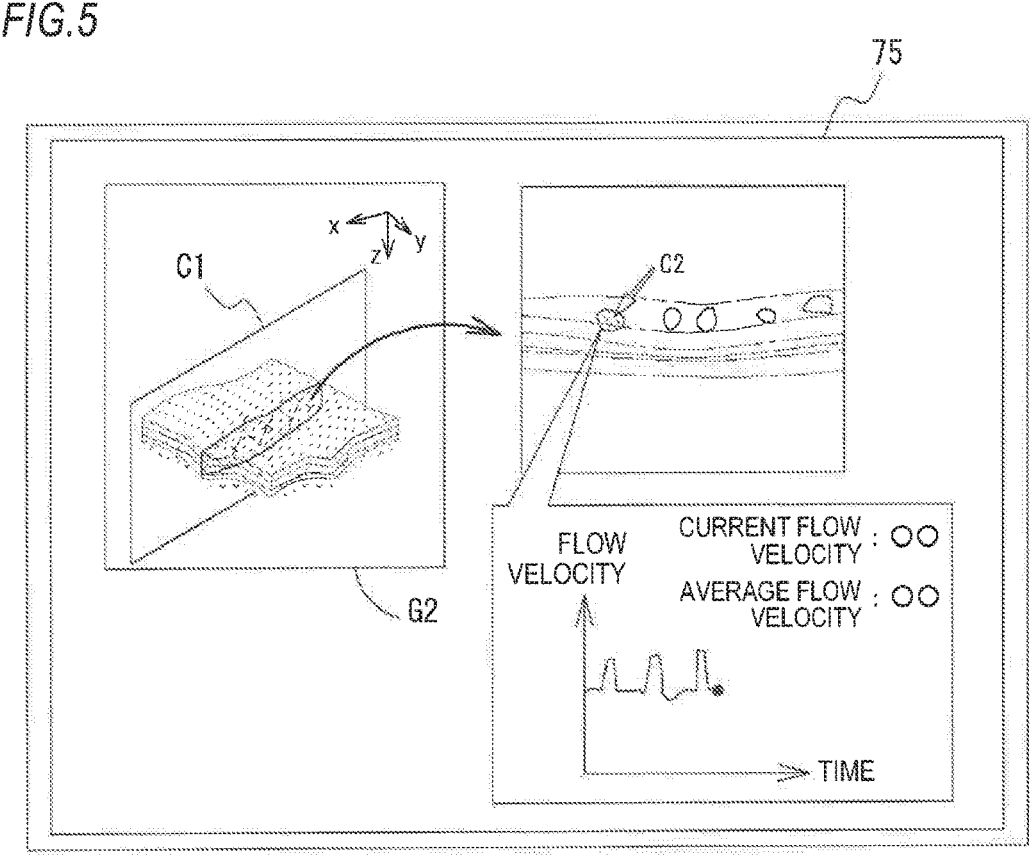
FIG. 5 is a schematic diagram illustrating a display example on a monitor.

For example, as illustrated in FIG. 5, the control unit 70 may display a three-dimensional image G1 based on three-dimensional OCT data on the monitor 75 in advance. The three-dimensional image G1 is used to check a position of a section displayed as a tomographic image when an examiner operates the operation unit 74. The examiner may designate a position of a section on the three-dimensional image G1 by operating a pointing device (one kind of the operation unit 74). In the example illustrated in FIG. 5, for example, a position of a cursor C1 moved on the three-dimensional image G1 is displaced in response to an operation on the operation unit 74. In this example, a section for acquiring a tomographic image is defined according to a position of the cursor C1. For example, the cursor C1 illustrated in FIG. 5 simulates a section, and a tomographic image of the section is displayed. In the example illustrated in FIG. 5, the cursor C1 is translated and rotated in response to an operation on the operation unit 74. Consequently, the examiner can designate a desired section.

<Process of Displaying Front Image>

Graphics obtained by visualizing three-dimensional OCT data may be, for example, a front image based on the three-dimensional OCT data. The front image based on the three-dimensional OCT data is obtained by integrating a signal intensity distribution in the depth direction at each xy position of the three-dimensional OCT data in a Z direction (so-called integrated image). Of course, the front image may be acquired through a process which is different from the integration process. For example, the front image may be acquired on the basis of some data regarding a depth direction in the three-dimensional OCT data. Such a front image may be front views regarding some layers forming the fundus (for example, which may be an image regarding a retinal surface layer illustrated in FIG. 4 and may be images regarding layers other than the surface layer), or may be a front view at a predetermined depth (for example, a C-scan image indicating a signal intensity distribution at a predetermined depth position). In a case where front views regarding some layers are acquired, the control unit 70 performs a division process on three-dimensional OCT data so as to specify a boundary of each layer. A front image is formed on the basis of information regarding the boundary portion specified through the division process.

A front image based on three-dimensional OCT data may be a motion contrast image.

Figure 4:
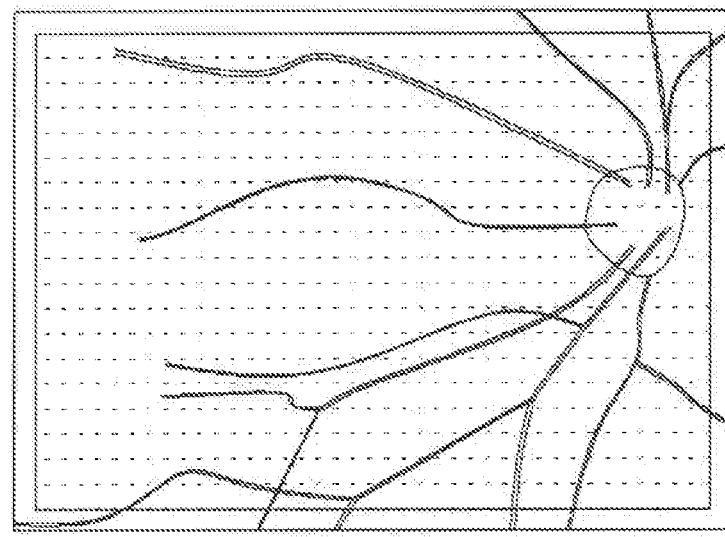
FIG. 4 is a schematic diagram illustrating a front image based on three-dimensional OCT data.

A front image is not limited to a two-dimensional display aspect (that is, an aspect in which the xy directions on the fundus are correlated with vertical and horizontal directions on the image) illustrated in FIG. 4. For example, a front image may be displayed in an aspect in which a three-dimensional shape of a layer is reflected. In other words, a front image may be displayed in a curved shape. In this case, the front image may be such graphics that some layers are diagonally viewed.

As mentioned above, in a case where a front image is displayed in real time on the monitor 75, a front image of a tissue located at any depth may be displayed as the front image. A position of a location displayed as a front image in the depth direction may be defined in advance. A position of a location displayed as a front image in the depth direction may be a position selected by the control unit 70 on the basis of a signal from the operation unit 74 (selection process). The signal from the operation unit 74 may be a signal for designating a position desired by the examiner. As a result of a position in the depth direction being selected on the basis of the signal from the operation unit 74, a front image for the selected position corresponding to the selected position is displayed on the monitor 75 by the control unit 70. Thus, a state of a tissue at the position desired by the examiner can be observed from a real-time front image.

Meanwhile, as described above, a front image based on three-dimensional OCT data may be at least a front image of some layers forming the fundus and a front image at a predetermined depth.

In a case where a front image is a front image of some layers, the control unit 70 selects any one of a plurality of layers forming the fundus, and displays a front image of the selected layer. More specifically, boundaries of a plurality of layers forming the fundus may be detected by performing a division process on three-dimensional OCT data, and any one of the detected boundaries may be selected. In the above-described way, a position of a location displayed as a front image in the depth direction may be selected. The control unit 70 may form a front image of a selected layer, and display the front image on the monitor 75.

On the other hand, in a case where a front image based on three-dimensional OCT data is a front image at a predetermined depth, the control unit 70 may select any one of coordinates in the depth direction in an acquisition range of the three-dimensional OCT data in the depth direction so as to select a position of a location displayed as a front image in the depth direction. A front image (for example, a C-scan image) representing a horizontal plane at the selected coordinate in the depth direction may be formed so as to be displayed on the monitor 75.

Here, with reference to FIG. 6, a description will be made of a specific example of an operation of the device in a case where a position of a location displayed as a front image in the depth direction, based on three-dimensional OCT data, is selected on the basis of a signal from the operation unit 74.

Figure 6:
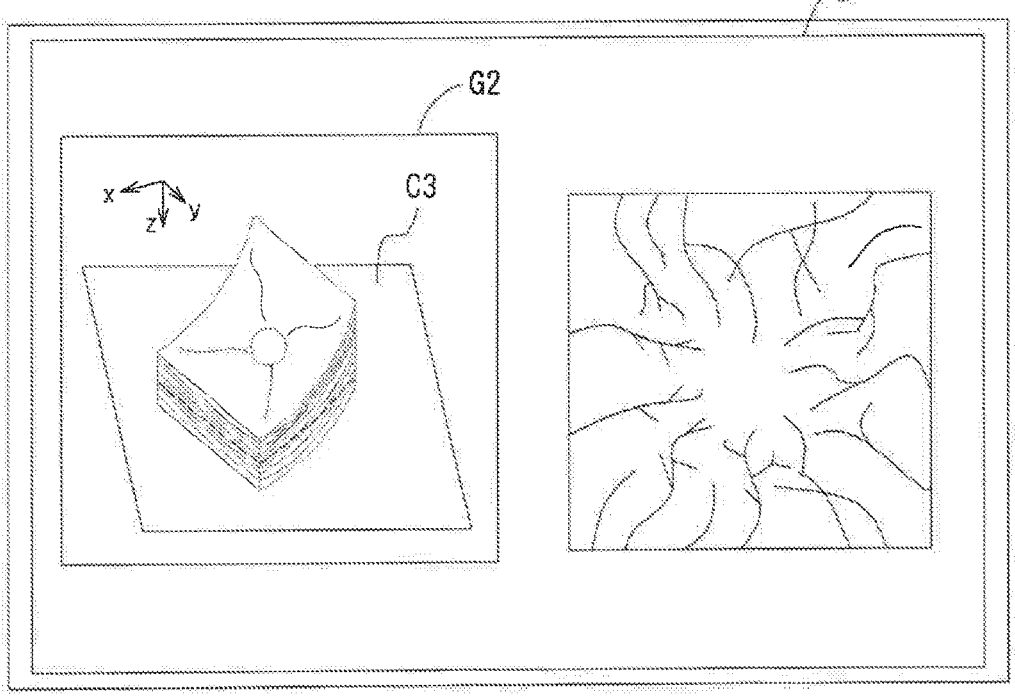
FIG. 6 is a schematic diagram illustrating another display example.

For example, as illustrated in FIG. 6, the control unit 70 may display graphics G2 indicating an acquisition range of three-dimensional OCT data in the depth direction on the monitor 75 in advance. The graphics G2 is used to check a position (a position in the depth direction) of a tissue desired to be displayed in a front image when the examiner operates the operation unit 74. In the example illustrated in FIG. 6, the graphics G2 uses a three-dimensional image of the subject's eye. The examiner may designate a location displayed as a front image on the graphics G2 by operating a pointing device (one kind of the operation unit 74). In the example illustrated in FIG. 6, for example, a position of a cursor C3 moved in the graphics G2 in the depth direction is displaced with respect to the graphics G2 in response to an operation on the operation unit 74. In this case, a location displayed as a front image is defined according to a position of the cursor C3. More specifically, a front image at which the cursor C3 is disposed in the depth direction is generated by the control unit 70 so as to be displayed on the monitor 75. In the example illustrated in FIG. 6, the cursor C3 simulates a horizontal plane (that is; a plane orthogonal to the depth direction) at a coordinate in the depth direction, and a front image corresponding to the horizontal plane is displayed.

The graphics G2 is not limited to a three-dimensional image, and may be replaced with other graphics such as a tomographic image obtained at any scanning line, a graph indicating a depth profile acquired at any point, and an indicator (for example, a number line).

A method of designating a section regarding a two-dimensional image is not limited to the above-described method. For example, the examiner may select a coordinate through which any curved surface passes via. a three-dimensional image displayed on the monitor 75 by using a pointing device, and thus a two-dimensional image having the curved surface as a section may be selected by the control unit 70.

However, examples of a three-dimensional image and a two-dimensional image are not limited to the above description. For example, a three-dimensional image is not limited to graphics obtained by visualizing the entire acquisition range of three-dimensional OCT data, and may be graphics obtained by selectively visualizing a region interposed between a first section in the acquisition range of three-dimensional OCT data and a second section which is different from the first section. Regarding the first section and the second section mentioned here, each section may be designated according to the same method as in a case of designating a section corresponding to a two-dimensional image, and the other section may be automatically set by designating one section. A three-dimensional image displayed in real time may be formed on the basis of any three-dimensional region in the acquisition range of three-dimensional OCT data, and is not limited to being formed on the basis of either of the entire acquisition range and a region surrounded by two sections.

In the three-dimensional OCT data, information regarding the region interposed between the first section and the differing second section may be averaged, for example, in a certain direction (for example, the depth direction) so that a two-dimensional image regarding the region interposed between the first section and the differing second section is formed by the control unit 70.

<Analysis Process on Three-Dimensional OCT Data>

In the present embodiment, the control unit 70 also performs various processes (for example, an analysis process and an image process) on three-dimensional OCT data. For example, the control unit 70 performs an analysis process on each piece of three-dimensional OCT data which is generated at any time. As a result, the control unit 70 outputs a real-time analysis result of the three-dimensional OCT data which is generated at any time. The term "output" here may be, for example, display output to the monitor 75. An analysis result may be output to an ophthalmologic surgery instrument (for example, an ophthalmologic surgery robot, an ophthalmologic laser surgery device, or an ophthalmologic laser photocoagulator) which is operated in parallel to imaging in the OCT 1. An analysis result output from the control unit 70 may be used as a signal for controlling an operation of the ophthalmologic surgery instrument (details thereof will be described later). First, a description will be made of a case where an analysis result is mainly output to the monitor 75 so as to be displayed.

An analysis process result may be obtained by processing at least two pieces of three-dimensional OCT data (that is, corresponding to two frames) among pieces of time-series three-dimensional OCT data. At least two pieces of three-dimensional OCT data mentioned here indicate pieces of three-dimensional OCT data acquired at different timings.

<Real-Time Display of Motion Contrast Image>

Three-dimensional motion contrast data of the subject's eye E may be acquired as a result of this process. For example, a moving image based on a motion contrast image which is a graphics obtained by visualizing the three-dimensional motion contrast data may be displayed on the monitor 75 as a result of the analysis process.

The three-dimensional motion contrast data is acquired by performing a plurality of raster scanning operations at different timings on a region where the fundus is located. More specifically, the control unit 70 acquires a complex OCT signal by performing Fourier transform on a signal (OCT signal) output from the detector 120. For example, the complex OCT signal is stored in the memory 72 when raster scanning is performed. Here, a complex OCT signal of one cycle of raster scanning is stored in the memory 72, and thus three-dimensional OCT data of one unit (in other words, one frame) is obtained. The control unit 70 processes complex OCT signals which are obtained at different timings of raster scanning at the same position (that is, the same xy coordinate), so as to obtain a profile in the depth direction at the xy coordinate. This process is performed for each position (that is, for each point or for each xy coordinate) where A-scan data is acquired, and thus three-dimensional motion contrast data in the range of raster scanning is acquired. As mentioned above, in the present embodiment, the three-dimensional motion contrast data is acquired as a result of processing at least two pieces of three-dimensional OCT data in which timings of raster scanning are different from each other.

Regarding a method of processing a complex OCT signal, for example, a method of calculating a phase difference of complex OCT signals, a method of calculating a vector difference of complex OCT signals, and a method of multiplying a phase difference of complex OCT signals by a vector difference are known, and any one thereof may be used. In the following description, the method of calculating a phase difference will be described as an example.

The three-dimensional motion contrast data obtained in the above-described way indicates, for example, a three-dimensional structure of a blood vessel. The control unit 70 may sequentially generate motion contrast images on the basis of three-dimensional motion contrast data, and may sequentially display the motion contrast images on the monitor 75. A graphics indicating a three-dimensional structure of a blood vessel may be displayed to overlap a three-dimensional OCT image (an image indicating a three-dimensional reflection intensity distribution as described above) by the control unit 70. Consequently, the three-dimensional structure of a blood vessel may be displayed on the monitor 75 in real time. Three-dimensional motion contrast data obtained in a time series is compared with three-dimensional motion contrast data obtained in the past, and thus a hemorrhage location generated in the middle of repeatedly acquiring three-dimensional OCT data can be detected. The detected hemorrhage location may be highlighted in the graphics indicating the three-dimensional structure of a blood vessel. For example, during surgery, a doctor or the like can promptly identify the hemorrhage location, and can thus immediately treat the hemorrhage.

<Analysis of Pulsation of Blood Flow>

In the analysis process on three-dimensional OCT data, an analysis process on pulsation of a blood flow may be performed. For example, the control unit 70 may further process a three-dimensional motion contrast image so as to acquire information regarding pulsation of a blood flow as a result of the analysis process. As specific examples, the information regarding pulsation of a blood flow may be information indicating any one of a direction of a blood flow, a velocity of a blood flow, a flow rate of a blood flow, pressure caused by a blood flow, and a pulse, and may be information indicating any one thereof in a time series.

As illustrated in FIG. 5, the process result may be displayed on the monitor 75 along with a graphics (in the example illustrated in FIG. 5, a three-dimensional image and a motion contrast image of a certain section) obtained by visualizing real-time three-dimensional OCT data. At this time, the control unit 70 may sequentially acquire a real-time process result corresponding to the graphics displayed on the monitor 75, and may display the process result on the monitor 75. In this case, at least the graphics obtained by visualizing three-dimensional OCT data and the process result corresponding to the graphics are displayed on the monitor 75. For example, a process result may be displayed in numerical values, may be displayed as a graph (for example, a trend graph) indicating a change over time of numerical values, and may be displayed in other aspects. As mentioned above, in the present embodiment, information regarding a blood flow useful for diagnosis can be obtained in real time in a wide range in which raster scanning is performed.

<Measurement of Blood Flow>

In the present embodiment, an absolute velocity of a blood flow may be obtained by using a three-dimensional structure of a blood vessel obtained on the basis of a three-dimensional motion contrast image and three-dimensional OCT data obtained through a plurality of raster scanning operations.

For example, a blood flow direction at each position and a diameter of a blood vessel at each position are obtained by using a three-dimensional structure of the blood vessel based on a three-dimensional motion contrast image. The blood flow direction of the blood vessel may be obtained by thinning a three-dimensional structure of the blood vessel as described above. The thinning may employ, for example, a morphology process, a distance conversion process, or an existing algorithm such as Hilditch or Deutsch.

Here, Doppler phase shift at each position is derived on the basis of three-dimensional OCT data which is obtained through a plurality of raster scanning operations. In this case, in a case where a predetermined raster scanning operation is repeatedly performed, a time interval in the Doppler phase shift may be set to integer multiple values of a cycle of raster scanning. The time interval is an interval of acquiring an OCT signal at the same position.

For example, a Doppler phase shift is obtained at the time interval of T on the basis of two pieces of three-dimensional OCT data which are obtained through two consecutive raster scanning operations, and a Doppler phase shift is obtained at the time interval of 2T on the basis of two pieces of three-dimensional OCT data which are obtained through two consecutive raster scanning operations after one cycle is skipped. In the above-described way, a Doppler phase shift may be obtained at a time interval set to an integer multiple of a cycle of raster scanning.

The control unit 70 obtains an absolute velocity of a blood flow at each position on the basis of the Doppler phase shift at each position of a blood vessel. In this case, in the Doppler phase shift at each position, a time interval may be constant, and may differ at each position. In a case where a time interval differs depending on a position, for example, the control unit 70 may determine a time interval according to information regarding a structure of a blood vessel at a point where a Doppler phase shift is obtained, and may obtain a Doppler phase shift at the time interval. The information regarding a structure of a blood vessel may be any one of a diameter of the blood vessel (blood vessel diameter), a direction of the blood vessel, and whether or not branching occurs.

A plurality of Doppler phase shifts at different time intervals may be obtained with respect to a single point, and an absolute velocity of a blood flow at the point may be obtained on the basis of the plurality of Doppler phase shifts.

In this Example, the control unit 70 may calculate an absolute velocity of a blood flow at each location of a blood vessel in real time. For example, an absolute velocity of a blood flow at each location may be calculated whenever three-dimensional OCT data based on new raster scanning (for convenience, first raster scanning) is obtained, on the basis of first three-dimensional OCT data based on the first raster scanning, second three-dimensional OCT data obtained at a first time interval corresponding to a time interval with the first three-dimensional OCT data, and third three-dimensional OCT data obtained at a second time interval corresponding to a time interval with the first three-dimensional OCT data (for example, including the time interval=T, 2T, 3T, . . . ).

A distribution of the absolute velocities at the respective locations obtained in the above-described way may be displayed as, for example, a color map on the monitor 75. The control unit 70 may compare an absolute velocity of a blood flow in a normal eye with an absolute velocity of a blood flow in the subject's eye E obtained through calculation. For example, the control unit 70 may obtain a difference between both of the absolute velocities, and may output difference information as, for example, numerical value information or a difference map. The absolute velocity of a blood flow in a normal eye may be stored in, for example, the memory 72 in advance.

The examiner may designate a position of a blood vessel at which an absolute velocity of a blood flow is calculated on an image (for example, any one of a three-dimensional motion contrast image, a tomographic image, and a front image based on three-dimensional OCT data) of the blood vessel displayed on a screen. For example, a location where an absolute velocity of a blood flow is calculated in an image displayed on the monitor 75 may be designated on the basis of the examiner's operation on the operation unit 74. The examiner may designate a blood vessel in which an absolute velocity of a blood flow is desired to be obtained, on an image of the blood vessel by operating a pointing device (one kind of the operation unit 74). For example, in the example illustrated in FIG. 5, a position may be designated according to a position of a cursor C2 displaced in response to an operation on the operation unit 74. In this case, for example, the control unit 70 may calculate an absolute velocity of a blood flow at the designated location. Alternatively, an absolute velocity of a blood flow at each position may be calculated on the background, and a calculation result corresponding to a location designated by the examiner may be selectively output (displayed, for example). Also in this case, a comparison process on an absolute velocity of a blood flow in a normal eye may be performed as described above.

The calculation of an absolute velocity of a blood flow may be performed whenever three-dimensional OCT data based on new raster scanning is obtained, and thus a calculation result may be updated at any time. However, regarding a frequency of the calculation of an absolute velocity of a blood flow, the calculation is not limited to being performed whenever three-dimensional OCT data of one frame is acquired, and may be performed whenever three-dimensional OCT data of a plurality of frames is acquired.

A calculation result of an absolute velocity of a blood flow may be displayed on the monitor 75. A calculation result may be displayed, for example, in at least one of numerical values and a graphics.

Three-dimensional OCT data of a plurality of frames is not necessarily required to be obtained in order to analyze pulsation of a blood flow. For example, the control unit 70 controls the optical scanner 108 so as to repeatedly acquire two-dimensional OCT data regarding the same cross-section, and can thus acquire information regarding pulsation of a blood flow with respect to the cross-section. In this case, repeated scanning on the cross-section may be performed between raster scanning operations for acquiring three-dimensional OCT data. Consequently, it is possible to obtain information regarding pulsation of a blood flow in real time at the substantially same time with three-dimensional OCT data. Each scanning line may be repeatedly scanned for a predetermined number of times in raster scanning of one cycle, and thus a plurality of pieces of two-dimensional OCT data in which a scanning interval for a scanning line is short may be obtained with respect to the same cross-section. The control unit 70 may process the plurality of pieces of two-dimensional OCT data so as to analyze information regarding pulsation of a blood flow in each scanning line.

<Other Analysis Processes>

As described above, regarding an analysis process performed on three-dimensional OCT data acquired at any time, a description has been made of a specific example of a case where the process is performed by using at least two pieces of three-dimensional OCT data (that is, three-dimensional OCT data of two frames), but this is only an example. For example, an analysis process may be performed so that time-series three-dimensional OCT data may be processed for each frame.

<Real-Time Thickness Measurement>

For example, the control unit 70 may perform an analysis process related to a thickness on a tissue of the subject's eye E. The control unit 70 analyzes a thickness of a tissue of the subject's eye E on the basis of three-dimensional OCT data generated at any time. As an analysis result, information regarding the thickness may be output. A thickness of a tissue may be, for example, a layer thickness of the fundus, and may be a thickness of a tissue of the anterior chamber. A thickness at each position may be obtained through the analysis process, and, as an analysis result, a map which indicates a two-dimensional distribution of thicknesses of a tissue of the subject's eye in real time may be obtained. The map may be displayed on the monitor 75. The real-time thickness map may be used, for example, in a case where the examiner observes, in real time, a change of a thickness due to predetermined work of applying pressure to the subject's eye E, or surgery of influencing a thickness of a tissue, such as refraction correction surgery or cataract surgery. The surgery mentioned here may be surgery using an ophthalmologic laser surgery device, and, in this case, the OCT 1 may be provided with an ophthalmotonometer (for example, a tonometer) which applies pressure to the subject's eye E, or an ophthalmologic laser surgery device. Each device may be controlled so that pressure or laser light is applied while three-dimensional OCT data is continuously acquired in the OCT 1. The control unit 70 may output a thickness analysis result to the ophthalmologic laser surgery device in order to control irradiation with laser light in the ophthalmologic laser surgery device.

<Extraction of Information Regarding Coagulation Spot>

The control unit 70 may analyze a coagulation spot formed on the subject's eye by photocoagulation laser light on the basis of three-dimensional OCT data generated at any time, and may output at least one of information regarding a size of the coagulation spot and information regarding a position of the coagulation spot in the subject's eye E as a real-time analysis result. The coagulation spot is displayed as a region having luminance which is different from luminance of a peripheral tissue in a graphics (which may be a three-dimensional image, and may be a two-dimensional image indicating any section) obtained by visualizing three-dimensional OCT data acquired in real time, and can thus be detected through image processing on the graphics. At least one of size information of the detected coagulation spot and position information of the detected coagulation spot in the subject's eye E may be specified through image processing on the graphics. The size information may be information regarding at least one of a diameter of the coagulation spot, a length thereof in the depth direction, and a volume thereof. The position information may be information form specifying a position where the coagulation spot is formed in the subject's eye E, and may be numerical value information such as coordinate information. The position information may be image information, and, may be a graphics in which three-dimensional OCT data is visualized and a formation position of the coagulation spot is highlighted. Such information is output in real time as an analysis result.

For example, the OCT 1 performing the analysis process may rapidly obtain information for evaluating an irradiation result as an analysis process result after the irradiation with photocoagulation laser light is performed. Thus, workability in irradiation work of photocoagulation laser light may be improved by utilizing the analysis result.

In this case, the OCT 1 may be provided with a laser photocoagulator which irradiates the subject's eye E with laser light. The control unit 70 may control each portion so that laser light is applied while three-dimensional OCT data is continuously acquired in the OCT 1. The control unit 70 may output an analysis result regarding a coagulation spot to the laser photocoagulator in order to control irradiation with laser light in the laser photocoagulator.

<Analysis Process on Separation Situation of Layer of Fundus>

For example, the control unit 70 may perform an analysis process on separation of a layer of the fundus of the subject's eye E in real time. The analysis process is based on three-dimensional OCT data including the fundus in a data acquisition range being acquired by the OCT 1 as an analysis target. A separation location of layers forming the fundus may be analyzed on the basis of three-dimensional OCT data generated at any time, and information (referred to as separation location information) indicating at least one of the presence or absence of a separation location of layers and a position of the separation location as a result thereof (analysis result). Obtaining the separation location information in real time is useful for, for example, vitreous body surgery. Information indicating a position of a separation location is information for specifying the separation location in either or both of the xy directions and the depth direction. The information for specifying a separation location may be numerical value information indicating a position of the separation location in the depth direction, and may be information for specifying at least one of two layers separated from each other. In a case where the analysis process is applied to vitreous body surgery, a separation situation of at least an internal limiting membrane (ILM) may be obtained in real time as an analysis result.

The separation location information may be output to the monitor 75 so as to be displayed thereon. A portion corresponding to at least a separation location may be highlighted on a graphics (which may be a three-dimensional image, and may be a two-dimensional image indicating any section) in which three-dimensional OCT data is visualized. In order to differentiate respective layers from each other, a boundary of other layers may be highlighted in an aspect which is different from highlighting of the separation location.

If, if surgery of separating a layer is performed by a surgery robot, the control unit 70 may output separation location information (that is, an analysis result) to the surgery robot in order to control a separation operation in the surgery robot.

<Analysis Process on Gap Between Tissue of Subject's Eye and Instrument>

For example, the control unit 70 may analyze a gap between an instrument used for diagnosis, treatment, or surgery of the subject's eye E, and a tissue of the subject's eye E in the depth direction, on the basis of the above-described three-dimensional OCT data generated at any time, and may output information regarding the gap between the instrument and the tissue of the subject's eye E in real time as an analysis result. The analysis process is based on three-dimensional OCT data including the tissue of the subject's eye E and the instrument in a data acquisition range being acquired by the OCT 1 as an analysis target.

The instrument may include various instruments such as a probe, forceps, a microkeratome, and an injector such as an IOL. A tissue of the subject's eye in which a gap with the instrument is analyzed may be selected from among respective parts of the subject's eye E via, for example, the operation unit 74. A predefined tissue may be used (for example, either one of the cornea and the retina).

The analysis result of the gap between the tissue of the subject's eye and the instrument may be output to the monitor 75 so as to be displayed thereon. For example, numerical value information indicating the gap as a numerical value may be displayed, and a graphics of an indicator or the like may be displayed.

Meanwhile, in a case where the instrument is made of metal, measurement light is reflected from a surface (a surface on a light source side) of the instrument, and thus the entire shape of the instrument may not be detected from three-dimensional OCT data. In contrast, for example, dimension information (which may be specifically dimension information with the surface of the instrument from which measurement light is reflected as a reference) of the instrument may be acquired in advance, and a gap between the instrument and the tissue of the subject's eye E may be analyzed by using the dimension information. In this case, measurement light is blocked by the instrument, and thus a location may occur at which position information of a tissue cannot be obtained from three-dimensional OCT data. Position information of a tissue blocked by the instrument may be estimated (or complemented) according to various methods, and a gap between the tissue of the subject's eye and the instrument may be analyzed on the basis of the estimated position information. For example, the control unit 70 may complement data regarding a tissue blocked by the instrument in three-dimensional OCT data acquired at any time by using three-dimensional OCT data which is acquired in a state in which the tissue of the subject's eye is not blocked by the instrument, and may analyze a gap between the tissue and the instrument.

If the instrument is driven by a surgery robot or the like, the control unit 70 may output an analysis result regarding a gap with the instrument to the surgery robot in order to control motion of the instrument in the surgery robot.

<Modification Examples of Structure and Control of Optical Scanner>

In the description of the embodiment, as a principal Example, a description has been mainly made of a case where a resonant scanner is used as the optical scanner 108*a* for main scanning in FIG. 1, scanning with measurement light when the resonant scanner is moved forward and scanning with measurement light when the resonant scanner is moved backward are alternately performed (refer to FIG. 2). However, as described above, as an optical scanner for main scanning according to the present disclosure, various optical scanners other than the resonant scanner may be used. For example, as in a specific example which will be described later, a single or a plurality of galvanomirrors may be used as an optical scanner for main scanning. The galvanomirror has a feature that controllability and the degree of freedom in a scanning pattern are high, and a scanning speed thereof may be changed through control. The galvanomirror can be made available at relatively low cost.

Figure 7:
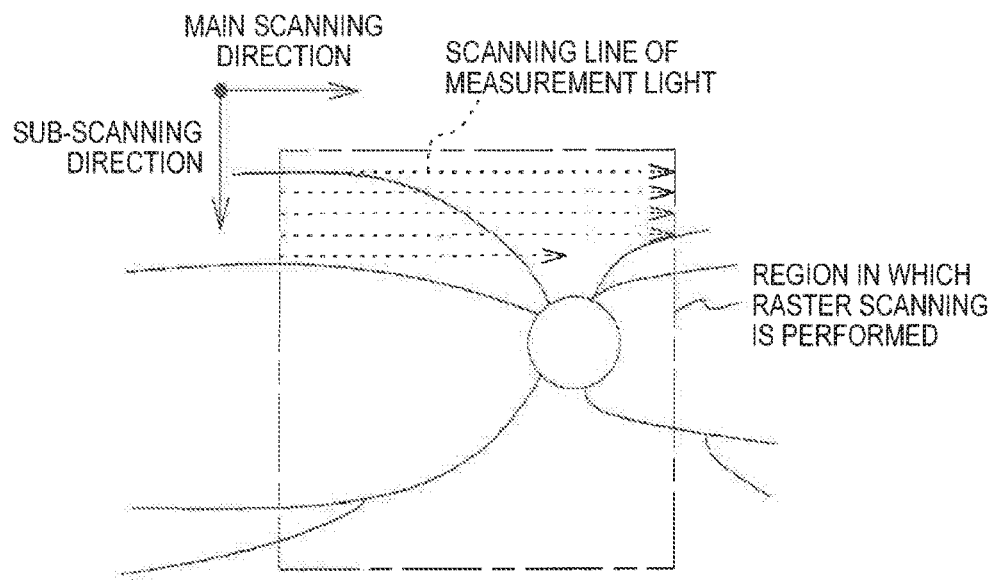
FIG. 7 is a diagram for explaining an example of second raster scanning.

In the description of the embodiment, a description has been mainly made of a case where the subject's eye is scanned with measurement light through raster scanning as illustrated in FIG. 2. However, any other configuration may be employed. For example, in the method illustrated in FIG. 2, in the optical scanner for main scanning, forward moving and backward moving are alternately performed, and scanning with measurement light is performed during each of forward moving and backward moving. In contrast, as in a specific example which will be described later, in a case where the optical scanner for main scanning performs a reciprocating operation, a method in which A-scan data is obtained on the basis of only forward moving of forward moving and backward moving may be employed (refer to FIG. 7). In this scanning method, a position where an A-scan operation is performed is hardly deviated relative to an adjacent scanning line compared with a method in which scanning with measurement light is performed during each of forward moving and backward moving (that is, a B-scan operation is performed). Here, an "operation of the optical scanner which moves an irradiation position of measurement light on the subject's eye in one direction" is defined as the "forward moving", and an "operation of the optical scanner which moves an irradiation position of measurement light on the subject's eye in a direction opposite to the one direction" is defined as the "backward moving". As a result, forward moving and backward moving may not uniquely defined depending on a design specification or an optical scanner or an optical system.

Of course, a method of irradiating the subject's eye with measurement light may employ scanning methods (for example, Lissajous scanning) other than raster scanning. In a case of Lissajous scanning, a reciprocating operation in a galvanomirror is not necessarily required to be performed as rapidly as in a case of raster scanning, and thus favorable scanning with measurement light can be easily performed by using the galvanomirror even if an acquisition cycle in an A-scan operation is 300 kHz or more. A scanning pattern of measurement light in Lissajous scanning may be, for example, a cycloidal form, a trochoidal form, or a spiral form, and may be other patterns. A scanning method of measurement light is not limited to two-dimensional scanning such as raster scanning and Lissajous scanning, and may be one-dimensional scanning.

Hereinafter, a description will be made of an Example in a case where a plurality of galvanomirrors are applied to an optical scanner for main scanning. In the following Example, unless otherwise mentioned, measurement light is assumed to be applied to the fundus. In description of this Example, the control unit 70 acquires A-scan data in a cycle of 300 kilohertz or more in the same manner as in the above-described Example. In the Example, the control unit 70 may control the galvanomirror as follows. In other words, the galvanomirror is repeatedly reciprocated with a constant swing angle, and thus scanning with measurement light is continuously performed twice or more in a main scanning direction. At this time, driving control is performed so that a time difference between start timings of the respective scanning operations is equal to or less than 5 milliseconds. A swing angle (the above-described "constant swing angle") of the galvanomirror corresponds to a distance of several millimeters on the fundus. For example, the swing angle may correspond to a distance of about 9 mm or more.

The control unit 70 may process A-scan data obtained through two or more scanning operations. In a case where scanning is repeatedly performed on a single scanning line, a data set including a plurality of pieces of A-scan data is acquired when the scanning line is scanned with measurement light once. The control unit 70 may process a plurality of data sets which are acquired in a time series with respect to a single scanning line. The process mentioned here may be, for example, a process of obtaining an addition image (the addition image includes an addition average image) of a tomographic image regarding a scanning line. The process may be a process of generating and acquiring an angiographic image (OCT angiography) regarding a scanning line.

In a case where a plurality of scanning lines are scanned with measurement light, the control unit may generate three-dimensional OCT data on the basis of A-scan data which is obtained by scanning the plurality of scanning lines with the measurement light. In this case, the control unit 70 controls driving of an optical scanner for sub-scanning along with the galvanomirror which is an optical scanner for main scanning.

<Example of Using Single Galvanomirror as Optical Scanner for Main Scanning>

Here, a description will be made of a specific example in which a single galvanomirror is provided as an optical scanner for main scanning.

In this specific example, OCT data is acquired on the basis of only forward moving of a reciprocating operation of the galvanomirror which is an optical scanner for main scanning.

Here, the galvanomirror may require a time period of at least 1 millisecond in each of the present state, forward moving, and backward moving. A reduction of the time required for one main scanning operation and positioning accuracy in an A-scan operation have a tradeoff relationship. Therefore, of a reciprocating operation of the galvanomirror, backward moving may be performed for a time period of about 1 millisecond, and forward moving may be performed for remaining time. In other words, if forward moving of the galvanomirror is performed in a range of about 1 millisecond to 4 milliseconds, a time difference between start timings of respective scanning operations can be made equal to or less than 5 milliseconds in a case where the galvanomirror is reciprocated at a constant swing angle. In a case where an acquisition cycle of A-scan data is assumed to be 300 kHz, A-scan data of about 300 points to 1200 points may be acquired in forward moving performed once by the galvanomirror.

There are following technical significances with respect to the fact that a time difference between start timings of respective scanning operations is equal to or less than 5 milliseconds.

For example, it becomes easier to acquire an OCT angiography in Which a blood vessel is favorably imaged. For example, the following Non-Patent Document 2 discloses a result that, in an OCT angiography of the fundus, a time interval is preferably set to a range of 1 millisecond to 5 milliseconds (more preferably, a range of 2.5 milliseconds to 5 milliseconds). Here, in a case where the galvanomirror is used as an optical scanner for main scanning, at least 2 milliseconds is required for the galvanomirror to be reciprocated once. Thus, in this Example, a time interval (a time difference between scanning start timings) can be realized in a range of 2 milliseconds to 5 milliseconds. The control unit 70 may control driving of the galvanomirror so that a time interval is set to a range of 2.5 milliseconds to 5 milliseconds.

In Non-Patent Document 2, a very short time interval such as 1 millisecond is realized according to a method called backstitched B-scans. In the backstitched B-scans method, in a case where a single scanning line is scanned with measurement light, the galvanomirror is returned little by little for a plurality of number of times so as to perform scanning in the way of being advanced twice and returned once. However, in this method, a time interval is required when the galvanomirror is returned little by little, and thus the time tends to be required for scanning per scanning line. In contrast, in this Example, since A-scan data is acquired at 300 kHz or more, OCT data of several hundreds or more of points per scanning line can be acquired at the above-described time interval even if a direction of the galvanomirror is not returned little by little during forward moving. In other words, a scanning operation of uniformly moving an irradiation position of measurement light with respect to a single scanning line is performed at least twice, and thus an OCT angiography regarding the scanning line can be obtained.

In other words, scanning for obtaining an OCT angiography can be realized at a higher speed while more simply controlling the galvanomirror than in a case of Non-Patent Document 2.

Non-Patent Document 2: "Angiography of the retina and the choroid with phase-resolved OCT using interval-optimized backstitched B-scans" Boy Braaf, Koenraad A. Vermeer, Kari V. Vienola, and Johannes F. de Boer; Optics Express Vol. 20, Issue 18, pp. 20516 to 20534 (2012)

For example, the influence of movement of the eye in each scanning operation is reduced. Movement of the eye such as involuntary eye movement during fixation has a tendency that amplitude (an amount of movement of the eye) is reduced as a cycle becomes shorter. For example, according to the following Non-Patent Document 3, amplitude is reduced to 0.5 arcmin (fundus 2.5 micrometers or less) in a region of 10 Hz or more. A single scanning operation on a single scanning line is performed for a time period of 1 millisecond to 4 milliseconds on the basis of forward moving of the galvanomirror, and thus a desired scanning line is easily scanned with measurement light with high accuracy.

Non-Patent Document 3: "Real-time eye motion compensation for OCT imaging with tracking SLO", Kari V. Vienola, Boy Braaf, Christy K. Sheehy, Qiang Yang, Pavan Tiruveedhula, David W. Arathorn, Johannes F. de Boer, and Austin Roorda; Biomedical Optics Express, Vol. 3, Issue 11, pp. 2950 to 2963, (2012)

It is considered that a time difference between start timings of respective scanning operations is also small even in a case where a response to a stimulus or a tissue change due to beating is observed. For example, an optical coherence elastography (OCE) is known, and there is an examination of observing deformation of a tissue based on a stimulus due to air puff. For example, in a case of the anterior chamber, deformation occurs within several milliseconds, and an elastic wave spreads widely. For example, in a case where the OCT 1 is used as an anterior chamber OCT, if the time required for each scanning operation is set to a range of 1 millisecond to 3 milliseconds, OCT data of the anterior chamber may be obtained in a scanning range and at a time interval, sufficient to observe deformation.

For example, in a case where raster scanning is performed, and three-dimensional OCT data is generated and acquired as a result thereof, A-scan data in a rectangular region having 256 or more points as one side in the xy directions and 512 or more points as the other side can be acquired on the basis of raster scanning for about one second or for a time point less than one second.

In the description of the above Example in which a resonant scanner is used as an optical scanner for main scanning, a description has been made of a case where a fast scanning operation is used to continuously acquire time-series three-dimensional OCT data, but, three-dimensional OCT data is not necessarily required to be continuously acquired. For example, the fast A-scan operation may be used to complete an operation of acquiring three-dimensional OCT data in a short period of time. In this case, an operation of acquiring three-dimensional OCT data may be started when a predetermined trigger signal is input to the control unit 70. The trigger signal may be input on the basis of a release operation performed by an examiner.

Meanwhile, a human blinking frequency is distributed centering on about 20 to 30 times although a personal difference is great (for example, refer to the following Non-Patent Document 4). In this Example, a range having the number several hundreds or more of points as one side can be scanned with measurement light in a time period which is sufficiently shorter than a time interval of blinking. As a result, a burden on a subject, such as eyelid opening, may be favorably reduced.

Non-Patent Document 4: "Studies on Blinking Times-(First) Blinking Times of Normal Adults"; Kumata MINAMI, Chikara YAMASHIRO, Mitsu MINAMI, Published Date 1957, Jul. 15; Clinical Ophthalmology Vol. 11, No. 7

For example, the control unit 70 may control driving of the galvanomirror so that the time required for forward moving to be performed once is equal to or less than 3 milliseconds. For example, in a case where A-scan data is acquired in a cycle of 300 kilohertz or more, if the time required for forward moving to be performed once is set to 3 milliseconds or less, 300 or more scanning lines are scanned with measurement light per second. In this case, driving of the galvanomirror is preferably controlled so that a single forward moving operation of the galvanomirror is preferably in a range of 2 milliseconds or more and 3 milliseconds or less. In this case, each A-scan operation can be performed at an expected position with favorable accuracy.

The control unit 70 may acquire A-scan data in a range of, for example, 350 kilohertz or more and 500 kilohertz or less. In this case, a speed of forward moving in the galvanomirror may be controlled in a range in which A-scan data of 1024 or more points can be acquired in a single forward moving operation. As an example, in a case where an acquisition cycle of A-scan data is about 400 kilohertz, three-dimensional OCT data having about 1024 points in the main scanning direction and about 512 points in the sub-scanning direction can be acquired through raster scanning for two seconds or less per cycle.

<Example of Using Two Galvanomirrors as Optical Scanner for Main Scanning>

In a case where a plurality of galvanomirrors are provided as an optical scanner for main scanning, deflection directions of the respective galvanomirrors used for main scanning are the same as each other. The respective galvanomirrors may be disposed on an optical path having no branch (serial arrangement), and may be disposed on a plurality of separate optical paths (parallel arrangement). In a case where three or more galvanomirrors are used as an optical scanner for main scanning, a combination of serial arrangement and parallel arrangement may be employed.

In a case where a plurality of galvanomirrors are provided as an optical scanner for main scanning, the time required for a single forward moving operation to be performed once in each galvanomirror may be set to the range described in the above.

<Example of using single galvanomirror as optical scanner for main scanning>

Figure 8:
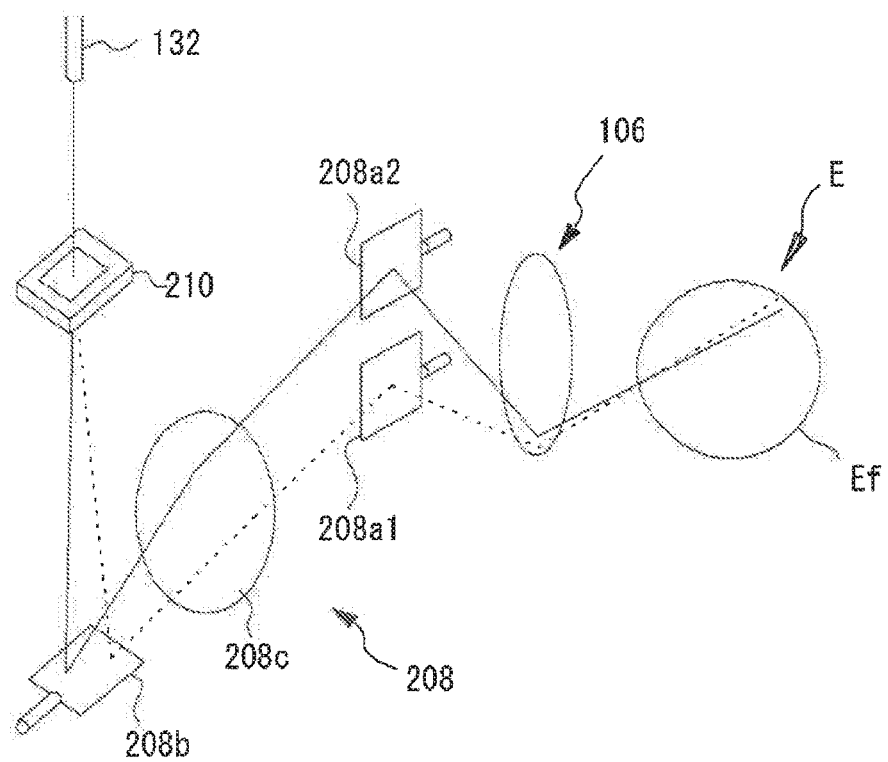
FIG. 8 is a diagram illustrating principal portions of an optical system related to a first modification example.
Figure 10:
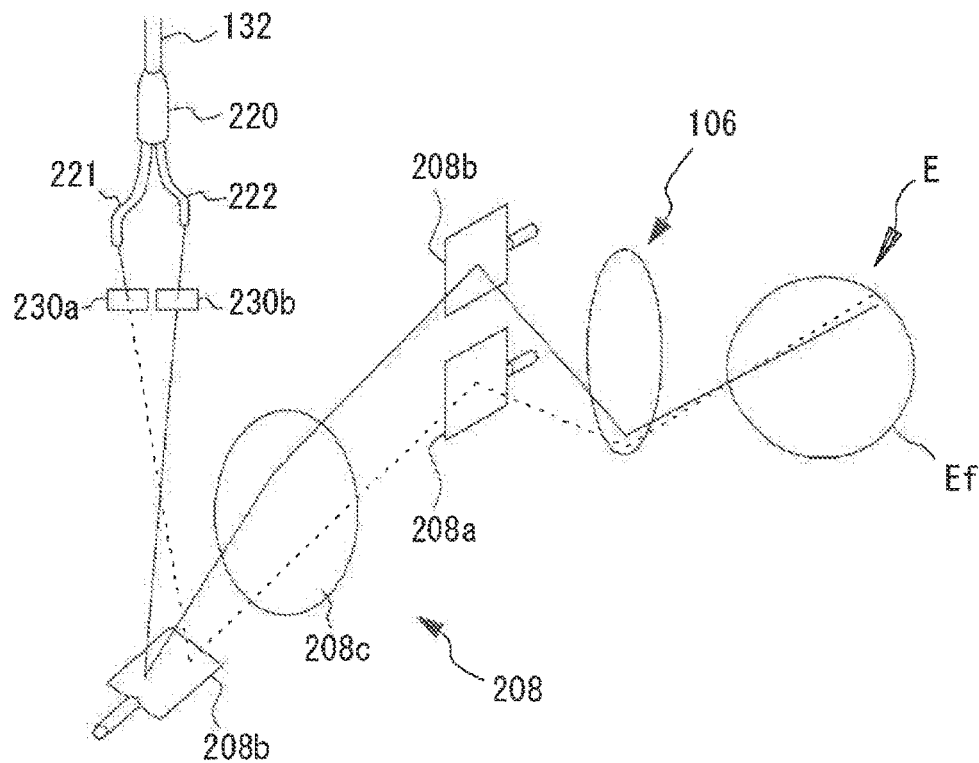
FIG. 10 is a diagram illustrating principal portions of the optical system related to a second modification example.
Figure 11:
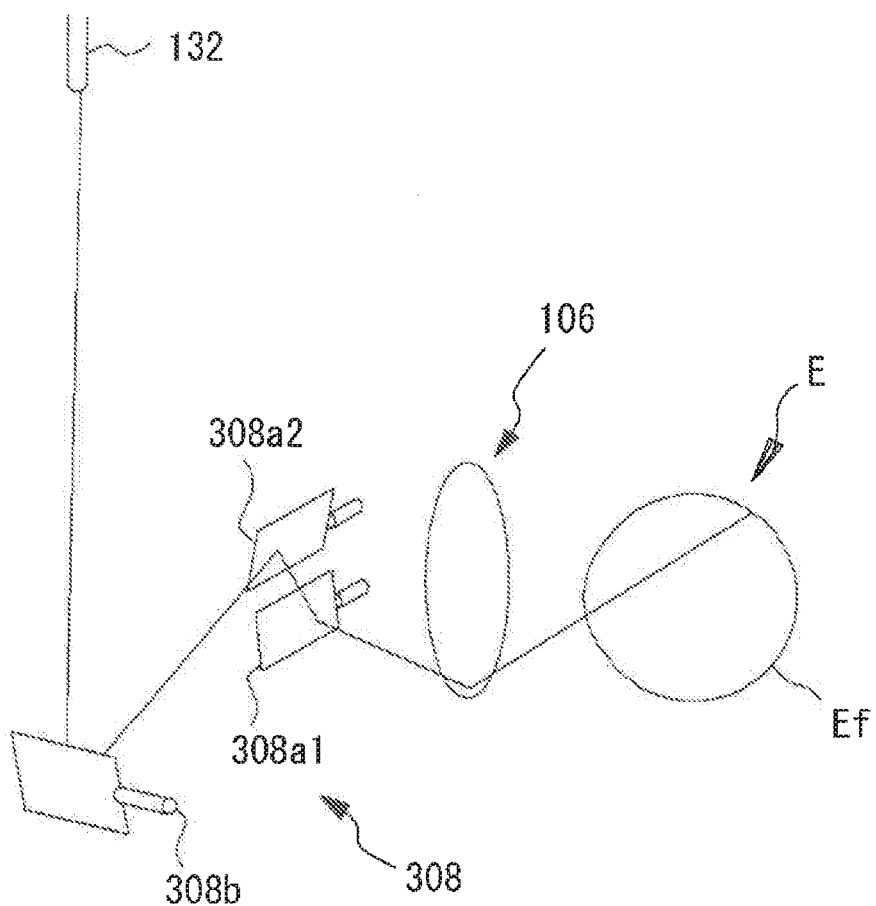
FIG. 11 is a diagram illustrating principal portions of the optical system related to a third modification example.

Here, FIGS. 8, 10 and 11 illustrate specific examples of a case where two galvanomirrors disposed in parallel or disposed in series are used as an optical scanner for main scanning. FIGS. 8, 10 and 11 respectively illustrate modification examples of the Example illustrated in FIG. 1. FIGS. 8, 10 and 11 illustrate an extracted part of the OCT optical system 100 as a principal difference from the Example illustrated in FIG. 1. In other words, there are differences between FIG. 1, and FIGS. 8, 10 and 11 in portions between the fiber 132 and the subject's eye E. In description of the modification examples, constituent elements common to the Example illustrated in FIG. 1 are given the same reference numerals in FIG. 1, and detailed description thereof will be omitted.

<Specific Modification Example (Parallel Arrangement) of Optical Scanner for Main Scanning>

First, a description will be made of a modification example illustrated in FIG. 8. In the modification example illustrated in FIG. 8, the OCT optical system 100 performs light scanning in two axes by using an optical scanner 208. The OCT optical system 100 in the modification example is provided with a light switch 210 (an example of a "light selection unit"). In FIG. 8, the light switch 210 is disposed between an emission end of the fiber 132 and the optical scanner 208. Measurement light having passed through the optical scanner 208 is applied to the subject's eye E via the objective optical system 106 as illustrated in FIG. 1.

The optical scanner 208 includes two galvanomirrors 208a1 and 208a2 as an optical scanner for main scanning. The optical scanner 208 is provided with an optical scanner 208b for sub-scanning. In FIG. 8, the galvanomirrors 208a1 and 208a2 are disposed further toward the subject's eye E side than the optical scanner 208b for sub-scanning. A lens 208c which deflects directions of measurement light beams which are respectively guided to the galvanomirrors 208a1 and 208a2 from the optical scanner 208b may be provided between the optical scanner 208b for sub-scanning and the galvanomirrors 208a1 and 208a2. In the following description, for convenience of the description, unless otherwise mentioned, scanning positions and scanning ranges on the subject's eye in both of the galvanomirrors 208a1 and 208a2 are assumed to match each other. The OCT optical system 100 has reference optical paths corresponding to the respective galvanomirrors 208a1 and 208a2 so that information regarding depth bands which are the same as each other is presented in A-scan data based on measurement light beams having passed through the galvanomirrors 208a1 and 208a2. In this case, the reference optical paths are not required to be provided separately for the respective galvanomirrors 208a1 and 208a2, and may be used in common. In this case, measurement optical paths are formed so that optical path length differences between reference light and the measurement light beams having passed through the galvanomirrors 208a1 and 208a2 are the same as each other with respect to the two measurement light beams.

The light switch 210 as an example of a "light selection unit" is used to selectively guide measurement light to one of the two galvanomirrors 208a1 and 208a2 for main scanning. In other words, the light switch 210 switches between a state of selectively guiding measurement light to one of the two galvanomirrors 208a1 and 208a2 and a state of selectively guiding the measurement light to the other.

The light switch 210 exemplified in FIG. 8 changes a direction of light which passes through (transmitted through or reflected at) a switch main body, and thus changes an optical scanner to which measurement light is guided between the two galvanomirrors 208*a*1 and 208*a*2.

As an example of the light switch, there may be a non-mechanical beam steering such as an LCOS type spatial light modulator (SLM). For example, as the LCOS type SLM, there is a device which can change orientations of liquid crystal molecules in several tens of microseconds order. In other words, a state of the beam steering is changed for a time sufficiently shorter than the time required for scanning with measurement light using the galvanomirrors 208*a*1 and 208*a*2.

As the light switch, not only such a beam steering but also a so-called electronic type beam steering and a so-called mechanical type beam steering may be used as appropriate.

Here, with reference to a timing chart illustrated in FIG. 9, a description will be made of detailed operations of the two galvanomirrors 208*a*1 and 208*a*2 and the light selection unit (light switch 210).

Figure 9:
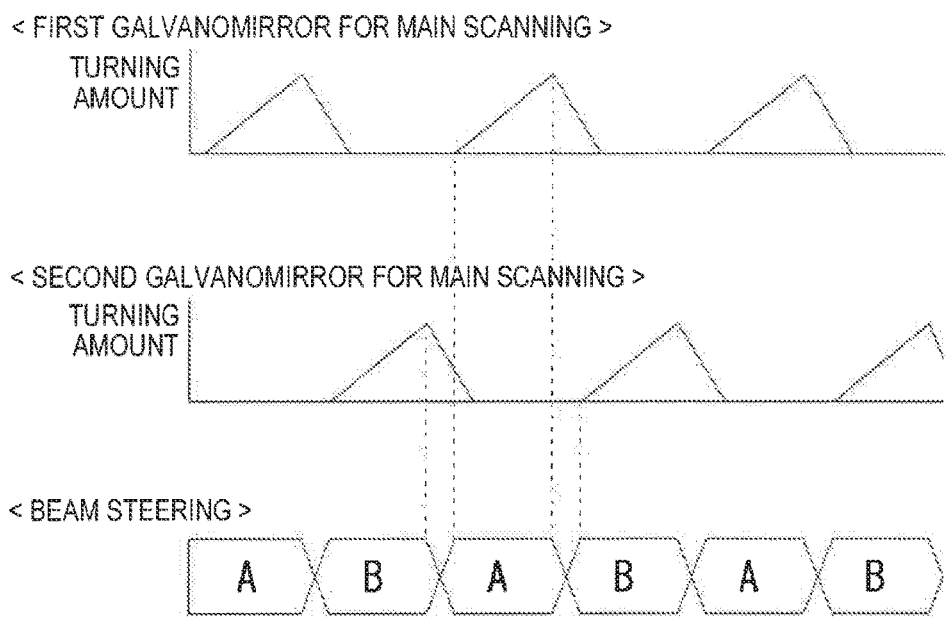
FIG. 9 is a timing chart illustrating operations of respective portions in the first modification example.

In FIG. 9, in a graph regarding the galvanomirrors 208*a*1 and 208*a*2, a period in which a turning quantity increases indicates a forward moving period, and a period in which the turning quantity decreases indicates a backward moving period.

In FIG. 9, two states of the light switch 210 are indicated by [A] and [B]. [A] indicates a state in which measurement light is guided to the galvanomirror 208*a*1 of the galvanomirrors 208*a*1 and 208*a*2, and [B] indicates a state in which measurement light is guided to the galvanomirror 208*a*2. States of the light switch 210 sequentially change in synchronization with reciprocating operations of the two galvanomirrors 208*a*1 and 208*a*2. In other words, the states of the light switch 210 are controlled so that measurement light is guided to the two galvanomirrors 208*a*1 and 208*a*2 in the forward moving periods.

As illustrated in FIG. 9, reciprocating operations of the two galvanomirrors 208*a*1 and 208*a*2 provided for main scanning are performed at different timings. In other words, the two galvanomirrors 208*a*1 and 208*a*2 alternately perform forward moving operations, and perform scanning with measurement light during the respective forward moving operations. At this time, in the timing chart illustrated in FIG. 9, one of the two galvanomirrors 208*a*1 and 208*a*2 selectively performs a forward moving operation, and performs scanning with measurement light. While one of the two galvanomirrors 208*a*1 and 208*a*2 performs a backward moving operation, the other starts to perform a forward moving operation. At this time, for example, a forward moving operation of one galvanomirror is completed, and a state changing operation is performed in the light switch 210, and then a forward moving operation of the other galvanomirror is started. However, in FIG. 9, for convenience of illustration, the time required to change a state of the light switch 210 is enlargedly illustrated, but, as described above, a state of the light switch 210 can be changed in a sufficiently short time with respect to forward moving and backward moving. Thus, a forward moving operation of the other may be started at a timing at which a forward moving operation of one of the two galvanomirrors 208*a*1 and 208*a*2 is completed, without taking into consideration the time required to change a state of the light switch 210. A backward moving operation of one of the two galvanomirrors 208*a*1 and 208*a*2 may be performed during a backward moving operation of the other galvanomirror, and, in this case, a forward moving operation of one galvanomirror is not necessarily required to be started at a timing at which a forward moving operation of the other galvanomirror is completed. For example, a forward moving operation may be started before a state of the light switch 210 is changed, so that a scanning speed of measurement light is stabilized.

As a result of the operation, measurement light can be applied through a forward moving operation of the other of the two galvanomirrors 208*a*1 and 208*a*2 in a backward moving period of one thereof. Consequently, it is possible to reduce the time required for an operation of acquiring three-dimensional OCT data or an OCT angiography.

For example, in a case where an acquisition cycle of A-scan data is about 400 kilohertz, if a forward moving operation of each of the galvanomirrors 208*a*1 and 208*a*2 is performed for about 2.5 milliseconds, three-dimensional OCT data having about 1000 points as a side in the main scanning direction is obtained. If raster scanning is performed for about one second (one second due to rounding off) per cycle, 1024 points is obtained as a side in the main scanning direction, 512 points is obtained as a side in the sub-scanning direction, and thus three-dimensional OCT data which is easily processed at a high speed can be acquired.

Next, a modification example illustrated in FIG. 10 will be described. In the modification example illustrated in FIG. 10, the light switch 210 in FIG. 8 is replaced with a differing device. The fiber 132 branches into a fiber 221 and a fiber 222 via a fiber beam splitter 220. Consequently, measurement light beams are simultaneously applied from emission ends of the fibers 221 and 222.

The measurement light emitted from the fiber 221 is guided to the galvanomirror 208*a*1, and the measurement light emitted from the fiber 222 is guided to the galvanomirror 208*a*2. Shutters 230*a* and 230*b* are disposed on emission lines of the measurement light beams from the respective fibers 221 and 222. In the present modification example, the shutters 230*a* and 230*b* are used a light switching unit. Opening and closing of the two shutters 230*a* and 230*b* are controlled to be alternately performed between the shutters 230*a* and 230*b*. More specifically, states of the two shutters 230*a* and 230*b* are controlled so that measurement light is guided to the two galvanomirrors 208*a*1 and 208*a*2 in the respective forward moving periods.

For example, Kerr cell shutters may be used as the shutters 230*a* and 230*b*. In this case, opening and closing operations can be performed at a high speed in a nanosecond level by using the Kerr effect. This is only an example, and various shutters may be used as the shutters 230*a* and 230*b*. Instead of the shutters, for example, a rotation slit may be provided on an emission line of measurement light from the fibers 221 and 222 as a light switching unit. One of measurement light beams from the respective fibers 221 and 222 passes through a slit of the rotation slit, and the other thereof is blocked by a light blocking member formed in the rotation slit. The rotation slit is rotated by a motor or the like, and thus measurement light is applied to the subject's eye in a switching manner.

<Specific Modification Example (Serial Arrangement) of Optical Scanner for Main Scanning>

Next, a modification example illustrated in FIG. 11 will be described. In the modification example illustrated in FIG. 11, the OCT optical system 100 performs light scanning in two axes by using an optical scanner 308. The optical scanner 308 includes two galvanomirrors 308*a*1 and 308*a*2 as an optical scanner for main scanning. The optical scanner 308 is provided with an optical scanner 308*b* for sub-scanning. In FIG. 11, the galvanomirrors 308a1 and 308a2 are disposed further toward the subject's eye E side than the optical scanner 308b for sub-scanning.

The two galvanomirrors 308a1 and 308a2 provided as an optical scanner for main scanning are disposed in series so that measurement light applied by one thereof is further applied by the other thereof. Consequently, a swing angle of measurement light can be increased compared with a case where only one of the two galvanomirrors 308a1 and 308a2 is driven.

In other words, the two galvanomirrors 308a1 and 308a2 are controlled so that forward moving operations and backward moving operations thereof are synchronized with each other. Turning directions in the forward moving operations and the backward moving operations match each other. As a result, measurement light applied by the galvanomirror 308a1 is further applied by the galvanomirror 308a2, and thus a scanning speed in the main scanning direction is increased compared with a case where only one of the two galvanomirrors 308a1 and 308a2 is driven.

Of the two galvanomirrors 308a1 and 308a2, the galvanomirror 308a2 disposed nearer to the subject's eye E may have a larger-sized mirror than the galvanomirror 308a1. If measurement light is applied by the galvanomirror 308a1, a passing range of the measurement light may be wider at a position of the galvanomirror 308a2 than at a position of the galvanomirror 308a1, but, even in this case, the galvanomirror 308a2 reliably easily reflects the measurement light.

The control unit 70 is not necessarily required to control turning speeds of the two galvanomirrors 308a1 and 308a2 to match each other. For example, of the two galvanomirrors 308a1 and 308a2, one thereof disposed nearer to the subject's eye may be driven at a higher speed than the other thereof. As described above, of the two galvanomirrors 308a1 and 308a2, a size of one thereof disposed nearer to the subject's eye may be larger than that of the other thereof. Since an operation can be performed at a higher speed as a size of the mirror becomes smaller, of the two galvanomirrors 308a1 and 308a2, one thereof disposed nearer to the subject's eye may be driven at a higher turning speed than the other thereof, and thus scanning speeds of the two galvanomirrors 308a1 and 308a2 may be heightened.

As mentioned above, the embodiment has been described, but the present disclosure may be variously modified without being limited to the embodiment.

For example, in relationships with necessary smoothness of a moving image, measurement accuracy, analysis accuracy, and the like as results of the above-described various processes, a frame rate, a resolution of an image (that is, the number of points in each direction), or both thereof are expected to require values greater than the exemplified values or to satisfactorily have smaller values. Thus, the exemplified values may be changed as appropriate in relationships with necessary measurement accuracy and analysis accuracy. For example, the technique of the present disclosure may be applied to a device in which an acquisition cycle of A-scan data is less than 300 kilohertz in a range in which a predetermined effect can be achieved.

In the above-described embodiment, a description will be made of only a case where three-dimensional OCT data regarding the fundus of the subject's eye is processed, but this is only an example. The technique of the present disclosure may be applied to a device which acquires three-dimensional OCT data regarding a part or the whole of the subject's eye. The technique of the present disclosure may be applied to an OCT device which acquires three-dimensional OCT data regarding, for example, the anterior chamber. The technique of the present disclosure may be applied to an OCT device which acquires three-dimensional OCT data regarding each position between the anterior chamber and the fundus.

In the modification examples illustrated in FIGS. 8 and 9, a description has been made of a case where information regarding depth bands which are the same as each other is presented in A-scan data based on measurement light beams having passed through the galvanomirrors 208a1 and 208a2, but information regarding depth bands which is different from each other may be presented. In this case, a difference between the depth bands may correspond to a difference between an optical path length difference between reference light and measurement light (hereinafter, referred to as first measurement light) having passed through the galvanomirror 208a1 and an optical path length difference between the reference light and measurement light (hereinafter, referred to as second measurement light) having passed through the galvanomirror 208a2. In other words, reference optical paths having different lengths may be provided to correspond to the galvanomirrors 208a1 and 208a2, and lengths of a measurement optical path may be different from each other in cases where measurement light passes through the galvanomirror 208a1 and the galvanomirror 208a2.

Focusing positions may be different from each other between measurement light beams respectively having passed through the galvanomirrors 208a1 and 208a2. For example, of the two galvanomirrors 208a1 and 208a2, measurement light having passed through one thereof is focused on the retinal surface (an example of a first focusing position), and measurement light having passed through the other thereof may be focused at a position (an example of a second focusing position) nearer to the choroid coat. With this configuration, the entire observation range in the retina can be observed with high sensitivity.

For example, at least one of a scanning speed of measurement light in raster scanning and a size of a region scanned with measurement light may be changed for each raster scanning operations by the control unit 70.

As a scanning speed of measurement light becomes higher, and a region scanned with the measurement light on the subject's eye becomes larger, an amount of the measurement light applied to the subject's eye can be increased while satisfying the light safety. Therefore, for example, the control unit 70 may change an amount of the measurement light according to an amount of a changed scanning speed in a case where at least one of a scanning speed of the measurement light and a size of a region scanned with the measurement light is changed. In this case, the control unit 70 may adjust a light amount by controlling output from a light source. The control unit 70 may control an amount of measurement light applied to the subject's eye by controlling a member provided on an emission optical path of the measurement light. For example, a fiber attenuator (attenuator) may be provided, and the fiber attenuator may control an attenuation amount. An aperture or a filter which is attachable and detachable on an optical path, or an aperture whose opening diameter is changeable may be provided on the optical path, and a light blocking amount may be changed by the aperture or the filter.

A scanning range (referred to as a "first scanning range") of measurement light (referred to as "first measurement light") having passed through the galvanomirror 208a1 and a scanning range (referred to as a "second scanning range") of measurement light (referred to as "second measurement light") having passed through the galvanomirror 208a2 may be different from each other.

Swing angles and driving speeds of the galvanomirrors 208a1 and 208a2 may be controlled by the control unit 70 so that the first scanning range is narrower than the second scanning range in at least the main scanning direction, and an acquisition position interval of A-scan data in the first scanning range is shorter than in the second scanning range. For example, the galvanomirror 208a1 may be turned at a lower swing angle and a lower angular velocity than the galvanomirror 208a2 so that the above-described scanning state is realized.

In a case where the first scanning range is different from the second scanning range, for example, the first scanning range and the second scanning range may be set by the control unit 70 so that the first scanning range is a range (for example, the optic papilla) including the lamina cribrosa, and the second scanning range is a range including the first scanning range. Consequently, detailed thickness information of the lamina cribrosa and layer thickness information of the fundus in the vicinity of the lamina cribrosa can be quickly obtained. In other words, it is possible to favorably obtain information useful for diagnosis of glaucoma.

In a case where the first scanning range is different from the second scanning range, an amount of the first measurement light may be different from an amount of the second measurement light. For example, an amount of the first measurement light may be smaller than an amount of the second measurement light. Consequently, it is possible to increase an S/N ratio of OCT data based on the first measurement light while satisfying the light safety.

Polarizations of measurement light (first measurement light) passing through the galvanomirror 208a1 and measurement light (second measurement light) passing through the galvanomirror 208a2 may be different from each other. The first measurement light and the second measurement light may have orthogonal polarization components. The control unit 70 may process a light reception signal from a detector based on the first measurement light and a light reception signal from a detector based on the second measurement light so as to acquire polarization OCT data. There are various methods of obtaining various pieces of information such as a degree of polarization uniformity (DOPU) tomographic image, a retardation or birefringence tomographic image, and an axis-orientation tomographic image on the basis of the polarization OCT data, and may be employed. For example, refer to JP-A-2013-148482.

In the above-described embodiment, a description has been made of a case where the OCT 1 is an SS-OCT which is one kind of the FD-OCT. However, the OCT 1 may be applied to other FD-OCTs. For example, the OCT 1 may be a spectral domain OCT (SD-OCT). In a case where the OCT 1 is the SD-OCT, the OCT 1 includes a light source which emits a light beam with a low coherent length, and a spectroscopic detector which detects an interference signal between reference light and return light of measurement light from the subject's eye for each wavelength component as a detector. OCT data of the subject's eye is obtained on the basis of the interference signal at each wavelength obtained by the spectroscopic detector. The technique of the present disclosure may be applied to OCT devices other than the FD-OCT (the SS-OCT, the SD-OCT, and the like).

<Other Aspects>

The present disclosure provides an optical coherence tomography device which can favorably acquire OCT data on the basis of scanning with measurement light using a galvanomirror according to the following first to twenty-first aspects.

(First Aspect)

An optical coherence tomography device includes an OCT optical system that irradiates a tissue of the subject's eye with measurement light from a light source, and detects interference between reference light and the measurement light reflected from the tissue by using a detector; a scanning unit that includes an optical scanner for main scanning that includes one or a plurality of galvanomirrors which scan the subject's eye with the measurement light in a predetermined main scanning direction by performing reciprocation driving formed of forward moving and backward moving, and an optical scanner for sub-scanning that is different from the optical scanner for main scanning in terms of a scanning direction, and scans the subject's eye with the measurement light in a two-dimensional manner on the basis of operations of the optical scanner for main scanning and the optical scanner for sub-scanning; and a processor, in which the processor acquires A-scan data based on a signal output from the detector in a cycle of 300 kilohertz or more, and in which the processor performs scanning with measurement light continuously twice or more in the main scanning direction by repeatedly reciprocating the galvanomirror at a constant swing angle, and controls at least the galvanomirror so that a time difference between start timings of respective scanning operations is set to a value which is equal to or less than 5 milliseconds.

(Second Aspect)

In the optical coherence tomography device according to the first aspect, the processor repeatedly scans the same scanning line with the measurement light by repeatedly reciprocating the galvanomirror at the constant swing angle, acquires a data set including a plurality of pieces of A-scan data when the scanning line is scanned with the measurement light once, and processes a plurality of data sets which are acquired in a time series with respect to a single scanning line.

(Third Aspect)

In the optical coherence tomography device according to the second aspect, the processor processes the plurality of data sets acquired in a time series so as to obtain an OCT angiography regarding the scanning line.

(Fourth Aspect)

In the optical coherence tomography device according to the third aspect, the processor controls the scanning unit so that the scanning line is repeatedly scanned with the measurement light in the same direction in respective scanning operations, and the time difference is set to a value which is 2.5 milliseconds or more and 5 milliseconds or less.

(Fifth Aspect)

In the optical coherence tomography device according to the first aspect, the processor scans a plurality of scanning lines whose scanning positions are different from each other in a sub-scanning direction with the measurement light, and generates three-dimensional OCT data on the basis of the A-scan data which is obtained by scanning the plurality of scanning lines with the measurement light.

(Sixth Aspect)

In the optical coherence tomography device according to any one of the first to fifth aspects, the processor controls the scanning unit so that scanning with the measurement light is performed during at least a forward moving operation of the galvanomirror, and a single forward moving operation is performed in a range of 2 milliseconds or more and 3 milliseconds or less.

(Seventh Aspect)

In the optical coherence tomography device according to the sixth aspect, the scanning unit includes a single galvanomirror as the optical scanner for main scanning, and the processor acquires the A-scan data in a range of 350 kilohertz or more and 500 kilohertz or less, and controls a forward moving speed of the galvanomirror in a range in which the A-scan data of 1024 or more points can be acquired through a single forward moving operation.

(Eighth Aspect)

In the optical coherence tomography device according to any one of the first to sixth aspects, the scanning unit includes at least a first galvanomirror and a second galvanomirror as the optical scanner for main scanning, and the processor performs scanning with the measurement light in the main scanning direction by driving a combination of the first galvanomirror and the second galvanomirror.

(Ninth Aspect)

In the optical coherence tomography device according to the eighth aspect, the first galvanomirror and the second galvanomirror independently scan the subject's eye with first measurement light which is measurement light passing through the first galvanomirror and second measurement light which is measurement light passing through the second galvanomirror.

(Tenth Aspect)

The optical coherence tomography device according to the ninth aspect, further includes a light selection unit that switches between a state in which measurement light from the light source is selectively guided to one of the first galvanomirror and the second galvanomirror and a state in which the measurement light is selectively guided to the other thereof, and the processor controls the light selection unit so that the first measurement light and the second measurement light are alternately applied to the subject's eye for respective scanning lines.

(Eleventh Aspect)

In the optical coherence tomography device according to the tenth aspect, the processor controls the first galvanomirror and the second galvanomirror so that the second galvanomirror performs forward moving in a backward moving period of the first galvanomirror, and the first galvanomirror performs forward moving in a backward moving period of the second galvanomirror, and further controls the light selection unit so that the subject's eye is scanned with the first measurement light on the basis of forward moving of the first galvanomirror, and the subject's eye is scanned with the second measurement light on the basis of forward moving of the second galvanomirror.

(Twelfth Aspect)

In the optical coherence tomography device according to any one of the ninth to eleventh aspects, the OCT optical system has a reference optical path corresponding to the first galvanomirror and a reference optical path corresponding to the second galvanomirror so that information regarding depth bands which are the same as each other is presented by using A-scan data based on the first measurement light and A-scan data based on the second measurement light.

(Thirteenth Aspect)

In the optical coherence tomography device according to any one of the ninth to twelfth aspects, the processor controls swing angles and driving speeds of the first galvanomirror and the second galvanomirror so that a first scanning range of the first measurement light is narrower than a second scanning range of the second measurement light in at least the main scanning direction, and an acquisition position interval of A-scan data in the first scanning range is shorter than in the second scanning range.

(Fourteenth Aspect)

In the optical coherence tomography device according to the thirteenth aspect, the processor sets the first scanning range to include the lamina cribrosa of the subject's eye, and further sets the second scanning range to include the first scanning range.

(Fifteenth Aspect)

In the optical coherence tomography device according to any one of the ninth to fourteenth aspects, the first measurement light and the second measurement light are different from each other in terms of polarization, and the processor processes a light reception signal from the detector based on the first measurement light and a light reception signal from the detector based on the second measurement light so as to obtain polarization OCT data.

(Sixteenth Aspect)

In the optical coherence tomography device according to any one of the ninth to eleventh aspects, the OCT optical system has a reference optical path corresponding to the first galvanomirror and a reference optical path corresponding to the second galvanomirror so that information regarding depth bands which are different from each other is presented by using A-scan data based on the first measurement light and A-scan data based on the second measurement light.

(Seventeenth Aspect)

In the optical coherence tomography device according to the eighth aspect, the first galvanomirror and the second galvanomirror are disposed in series so that light applied by one of the first galvanomirror and the second galvanomirror is further applied by the other thereof.

(Eighteenth Aspect)

In the optical coherence tomography device according to the seventeenth aspect, of the first galvanomirror and the second galvanomirror, a size of a mirror surface of one thereof disposed nearer to the subject's eye is larger than a size of a mirror surface of the other thereof.

(Nineteenth Aspect)

In the optical coherence tomography device according to the seventeenth or eighteenth aspect, the processor synchronously controls the first galvanomirror and the second galvanomirror so that a scanning speed in the main scanning direction is higher than in a case where only one of the first galvanomirror and the second galvanomirror is driven as a result of light applied by one of the first galvanomirror and the second galvanomirror being further applied by the other thereof.

(Twentieth Aspect)

In the optical coherence tomography device according to the nineteenth aspect, of the first galvanomirror and the second galvanomirror, the processor drives one thereof nearer to the subject's eye at a lower turning speed than the other thereof.

(Twenty-First Aspect)

In the optical coherence tomography device according to the first aspect, the processor scans the subject's eye with the measurement light on the basis of each of forward moving and backward moving of the galvanomirror, and further acquires A-scan data based on each scanning operation.

What is claimed is:

1. An optical coherence tomography device comprising:
   an OCT optical system configured to irradiate a tissue of a subject's eye with measurement light from a light source, the OCT optical system including a detector configured to detect interference between reference light and the measurement light reflected from the tissue and
   a processor configured to:
   a generation process of acquiring A-scan data based on a signal output from the detector in a cycle of 300 kilohertz or more and generating three-dimensional OCT data based on the acquired A-scan data; and an analysis process on each piece of the three-dimensional OCT data generated through the generation process, so as to output a real-time analysis result of the three-dimensional OCT data which is generated.

2. The optical coherence tomography device according to claim 1,
wherein the processor
displays a graphics in which the three-dimensional OCT data generated through the generation process is visualized on a monitor in real time, and
outputs to the monitor the analysis result corresponding to the graphics displayed on the monitor to display the analysis result on the monitor.

3. The optical coherence tomography device according to claim 2, wherein the processor forms a three-dimensional blood vessel image of the subject's eye through the analysis process, and displays the formed three-dimensional blood vessel image on the monitor in an overlapping manner with a three-dimensional image of the subject's eye obtained by visualizing the three-dimensional OCT data.

4. The optical coherence tomography device according to claim 1, wherein the processor generates pieces of time-series three-dimensional OCT data through the generation process, and obtains the analysis result by processing at least two pieces of three-dimensional OCT data among the pieces of time-series three-dimensional OCT data in the analysis process.

5. The optical coherence tomography device according to claim 4, wherein the processor generates three-dimensional motion contrast data regarding the subject's eye through the analysis process, and displays a moving image formed of a three-dimensional motion contrast image which is a graphics obtained by visualizing the three-dimensional motion contrast data, on the monitor as the analysis result.

6. The optical coherence tomography device according to claim 4, wherein the processor generates three-dimensional motion contrast data through the analysis process, and obtains information regarding pulsation of a blood flow in the subject's eye as the analysis result based on the three-dimensional motion contrast data.

7. The optical coherence tomography device according to claim 6, wherein the processor acquires the information regarding pulsation as the analysis result of the analysis process based on a blood flow direction based on the three-dimensional motion contrast data, and at least the two pieces of three-dimensional OCT data.

8. The optical coherence tomography device according to claim 7, wherein
at least the two pieces of three-dimensional OCT data include first three-dimensional OCT data, second three-dimensional OCT data having a time interval with the first three-dimensional OCT data as a first time interval, and third three-dimensional OCT data having a time interval with the first three-dimensional OCT data as a second time interval, and
the processor simultaneously obtains pieces of the information regarding pulsation at a plurality of locations in which diameters of blood vessels are different from each other based on a Doppler phase shift between the first three-dimensional OCT data and the second three-dimensional OCT data and a Doppler phase shift between the first three-dimensional OCT data and the third three-dimensional OCT data by performing the analysis process.

9. The optical coherence tomography device according to claim 1, wherein the processor analyzes a coagulation spot formed on the subject's eye by photocoagulation laser light based on the three-dimensional OCT data generated through the generation process by performing the analysis process, and outputs at least one of information regarding a size of the coagulation spot and information regarding a position of the coagulation spot in the subject's eye as the analysis result.

10. The optical coherence tomography device according to claim 1, wherein the processor generates the three-dimensional OCT data including the fundus of the subject's eye in a data acquisition range through the generation process, analyzes a separation location of layers forming the fundus based on the three-dimensional OCT data generated in the analysis process, and outputs separation location information which is information indicating at least one of the presence or absence of a separation location of layers and a position of the separation location as the analysis result.

11. The optical coherence tomography device according to claim 1, wherein the processor generates the three-dimensional OCT data including the subject's eye and an instrument used for diagnosis, treatment, or surgery of the subject's eye in a data acquisition range through the generation process, analyzes a gap between a tissue of the subject's eye and the instrument in a depth direction, based on the three-dimensional OCT data generated through the analysis process, and outputs information regarding the gap as the analysis result.

12. The optical coherence tomography device according to claim 1, wherein the processor analyzes a thickness of a tissue of the subject's eye by performing the analysis process on the three-dimensional OCT data generated through the generation process, and outputs information regarding the thickness as the analysis result.

13. The optical coherence tomography device according to claim 1, further comprising:
an input interface configured to receive an instruction from an examiner,
wherein the processor displays a graphics obtained by visualizing the three-dimensional OCT data generated through the generation process, on the monitor in real time, receives a region in which the analysis process is performed on the graphics based on a signal from the input interface, and displays a result of an analysis process on the region on the monitor.

14. The optical coherence tomography device according to claim 1, wherein the processor obtains an analysis result of a three-dimensional region included in an acquisition range of three-dimensional OCT data through the analysis process.

* * * * *